(12) United States Patent
Shochat et al.

(10) Patent No.: US 6,338,835 B1
(45) Date of Patent: *Jan. 15, 2002

(54) RADIOPROTECTANT FOR PEPTIDES LABELED WITH RADIOISOTOPE

(75) Inventors: Dan Shochat, Palo Alto, CA (US); Albert S. K. Chan, Ottawa (CA); Michael J. Buckley, Pleasanton; David Colcher, San Mateo, both of CA (US)

(73) Assignee: Coulter Pharmaceutical, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/453,985

(22) Filed: Dec. 2, 1999

Related U.S. Application Data

(63) Continuation of application No. PCT/US98/11428, filed on Jun. 3, 1998, and a continuation of application No. 08/918,525, filed on Aug. 21, 1997, now Pat. No. 5,961,955.
(60) Provisional application No. 60/048,387, filed on Jun. 3, 1997.

(51) Int. Cl.$^7$ .......................... A61K 51/00; A61M 36/14

(52) U.S. Cl. ..................... 424/1.69; 424/1.11; 424/1.65

(58) Field of Search ................................ 424/1.11, 1.65, 424/1.49, 1.69; 530/300; 534/7, 10–16

(56) References Cited

U.S. PATENT DOCUMENTS

| | | |
|---|---|---|
| 4,411,881 A | 10/1983 | Tzodikov |
| 4,421,735 A | 12/1983 | Haber et al. |
| 4,427,631 A | 1/1984 | Bunting et al. |
| 4,676,979 A | 6/1987 | Schellenberg et al. |
| 5,011,676 A | 4/1991 | Thakur |
| 5,384,113 A | 1/1995 | Deutsch et al. |
| 5,393,512 A | 2/1995 | Vanderheyden et al. |
| 5,514,363 A | 5/1996 | Shochat et al. |
| 5,595,721 A | 1/1997 | Kaminski et al. |
| 5,961,955 A | * 10/1999 | Shochat et al. ............ 424/1.69 |

FOREIGN PATENT DOCUMENTS

| | | |
|---|---|---|
| DE | 933885 | 10/1955 |
| EP | 0 111 414 | 6/1984 |
| EP | 0622082 | 11/1994 |
| RO | 103925 | 12/1991 |
| WO | WO 91/04057 | 4/1991 |
| WO | WO 93/02652 | 2/1993 |
| WO | WO 93/04702 | 3/1993 |
| WO | WO 93/22260 | 11/1993 |

OTHER PUBLICATIONS

Arimura et al., "Production of Antiserum to LH–Releasing Hormone (LH–RH) Associated with Gonadal Atrophy in Rabbits: Development of Radioimmunoassays for LH–RH," *Endocrinology*, 93 (5): 1092–93 (1973).

Barandun et al., "The Measurements of Gastro–intestinal Protein Loss by Means of I131–labelled Polyvinylpyrrolidone," Radioisotope Techniques in the Study of Protein Metabolism. Findings of a Panel Held in Vienna, Abstract No. 4473034 (1964).

Chapiro et al., "Formation of Poly(N–Vinylpyrrolidone) Gels by the Action of Gamma–Rays on Aqueous Solutions of Poly(N–Vinylpyrrolidone)," *Eur. Polym. J.*, 21 (1):49–53, Abstract No. 3159534 (1985).

Eisenberg et al., "Radioprotection of Sheep Erythrocytes by Polyvinyl Pyrrolidone," *Appl. Radiat. Isot.*, 38 (2) :147–148 (1987).

Faiz–Ur–Rehman et al., "Preparation of Sup(99m) Tc–Tin–Phosphate Polyvinyl Pyrrolidone Stabilized Colloid and Distribution in Bone Marrow," *Appl. Radiat. Isot.*, 37 (3) : 249–255, Abstract No. 3296699 (1986).

Gombotz et al., "The Stabilization of a Human IgM Monoclonal Antibody with Poly(vinylpyrrolidone)," *Pharmaceutical Research*, 11 (5) :624–632 (1994).

Kline Gordon M., "Technical Section: Polyvinylpyrrolidone," *Modern Plastics*, 23 (3) :157–161, 212, 214, 216, 218 (1945).

Rosiak et al., "Fast Reaction of Irradiated Polymers: Pt. 1. Crosslinking and Degradation of Polyvynylpyrrolidine," *Radiation Physics and Chemistry*, 36 (6) :747–755, Abstract No. 3934126 (1990).

Shaeffer et al., "Polyethylene Glycol as a Protector Against Head and Neck Irradiation," *Int. J. Oncology, Biology, Physics*, 10 (12) :2329–2333 (1984).

Stefanova et al., "Radioprotective Preparation," Abstract No. 4291719 (1988).

Wahl et al., "Inhibition of Autoradiolysis of Radiolabeled Monoclonal Antibodies by Cryopreservation," *The Journal of Nuclear Medicine*, 31 (1) :84–89 (1990).

* cited by examiner

Primary Examiner—Dameron L. Jones
(74) Attorney, Agent, or Firm—Cooley Godward LLP

(57) ABSTRACT

A method of ameliorating degradation radiolabeled peptides, especially radiolabeled proteins such as antibodies, by including povidone, also widely known as polyvinylpyrrolidone or PVP, as a radioprotectant in a composition containing a radiolabeled peptide is described. A radioprotectant composition and a stable peptide-radioisotope composition having povidone are also described. Ascorbic acid or other secondary stabilizers may also be added to the compositions to further enhance radioprotection.

23 Claims, 19 Drawing Sheets

VARIOUS % PVP AS A RADIOPROTECTANT
ROOM TEMPERATURE STORAGE

5a = MATERIAL STORED FROZEN, THAWED @ day 5
PRODUCT SPECIFICATION LIMIT: >95%

DRUG PRODUCT POTENCY- ROOM TEMPERATURE
EVALUATION OF DIFFERENT CONCENTRATIONS OF PVP

PRODUCT SPECIFICATION LIMIT : >65%

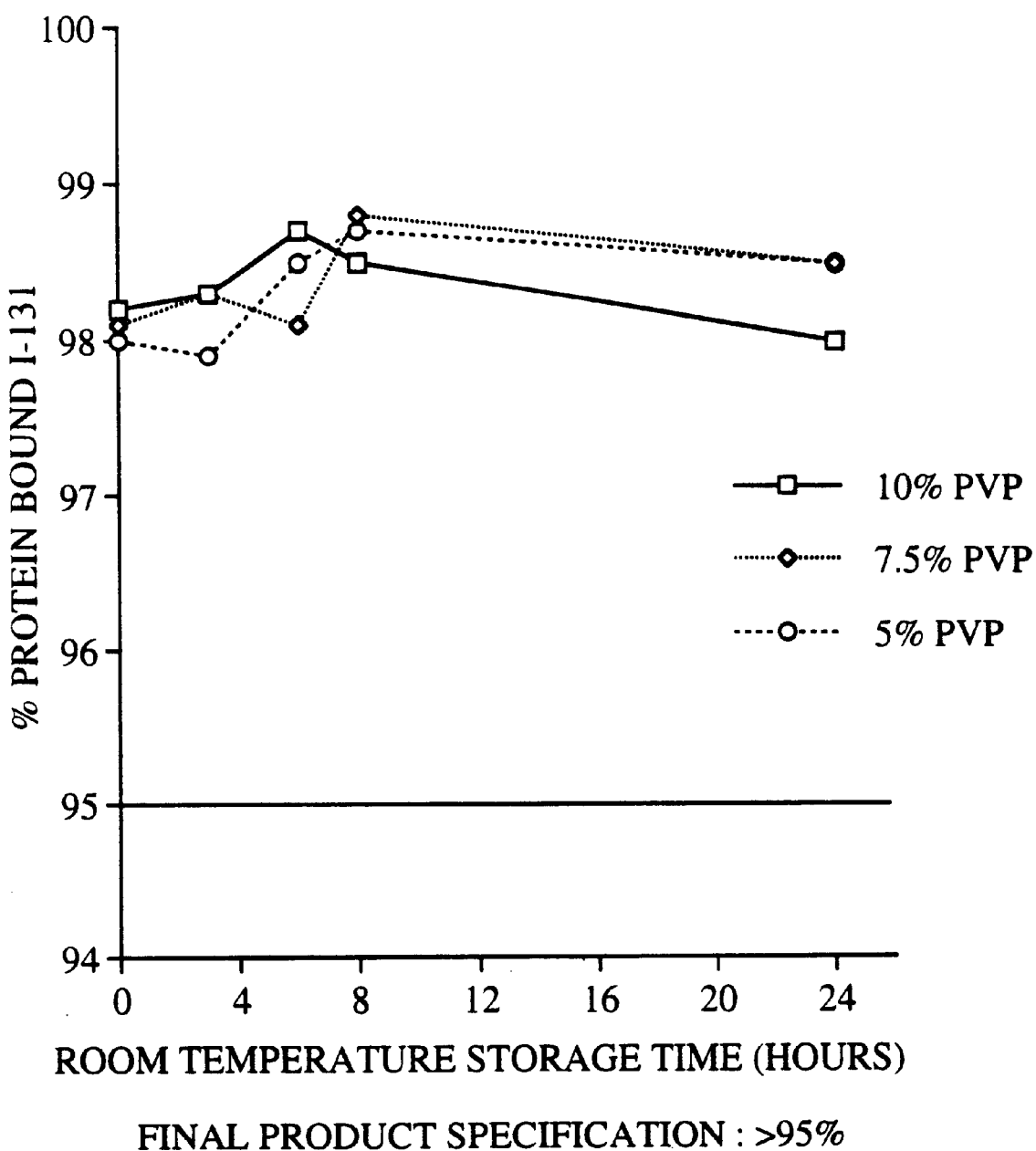

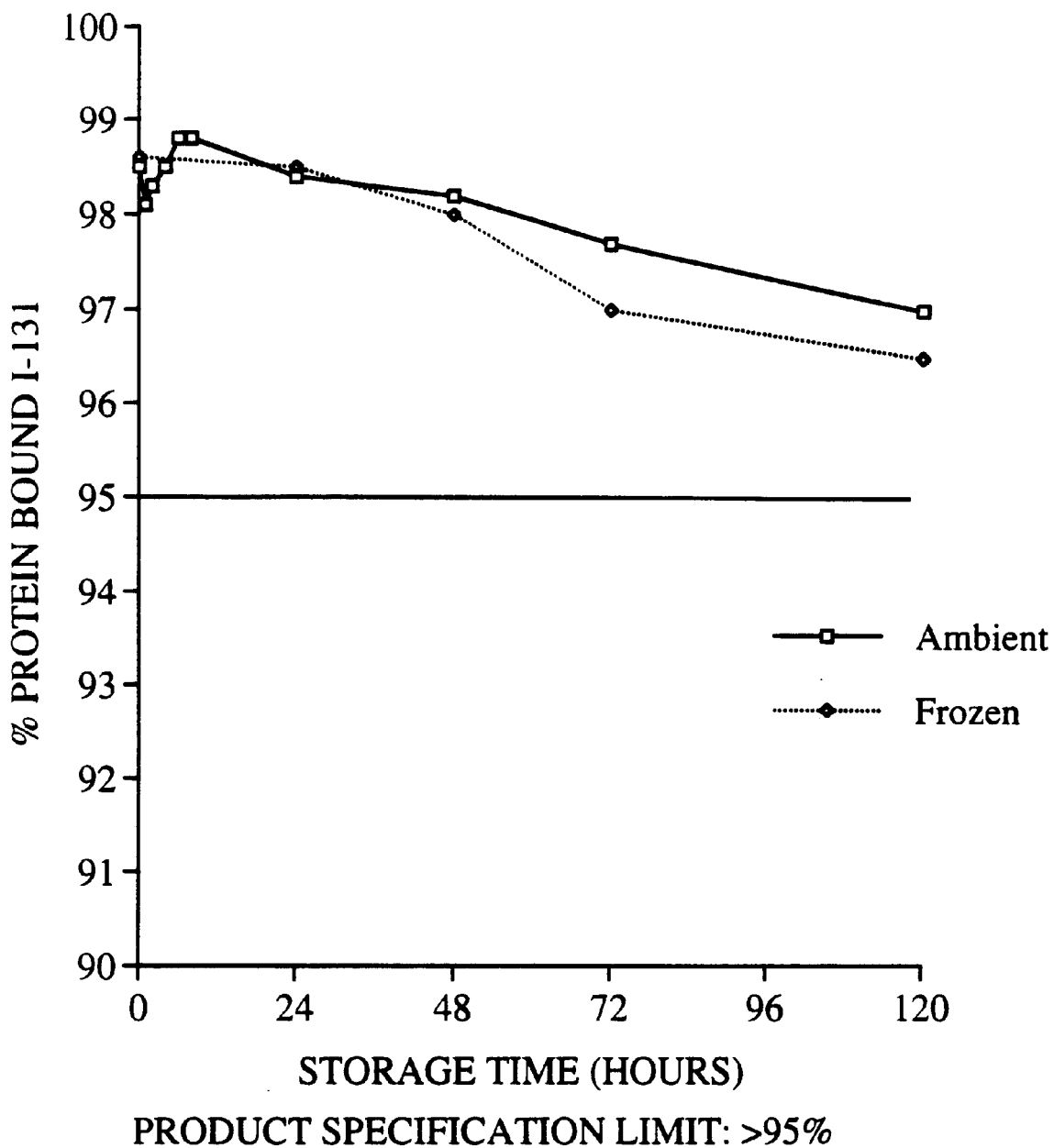

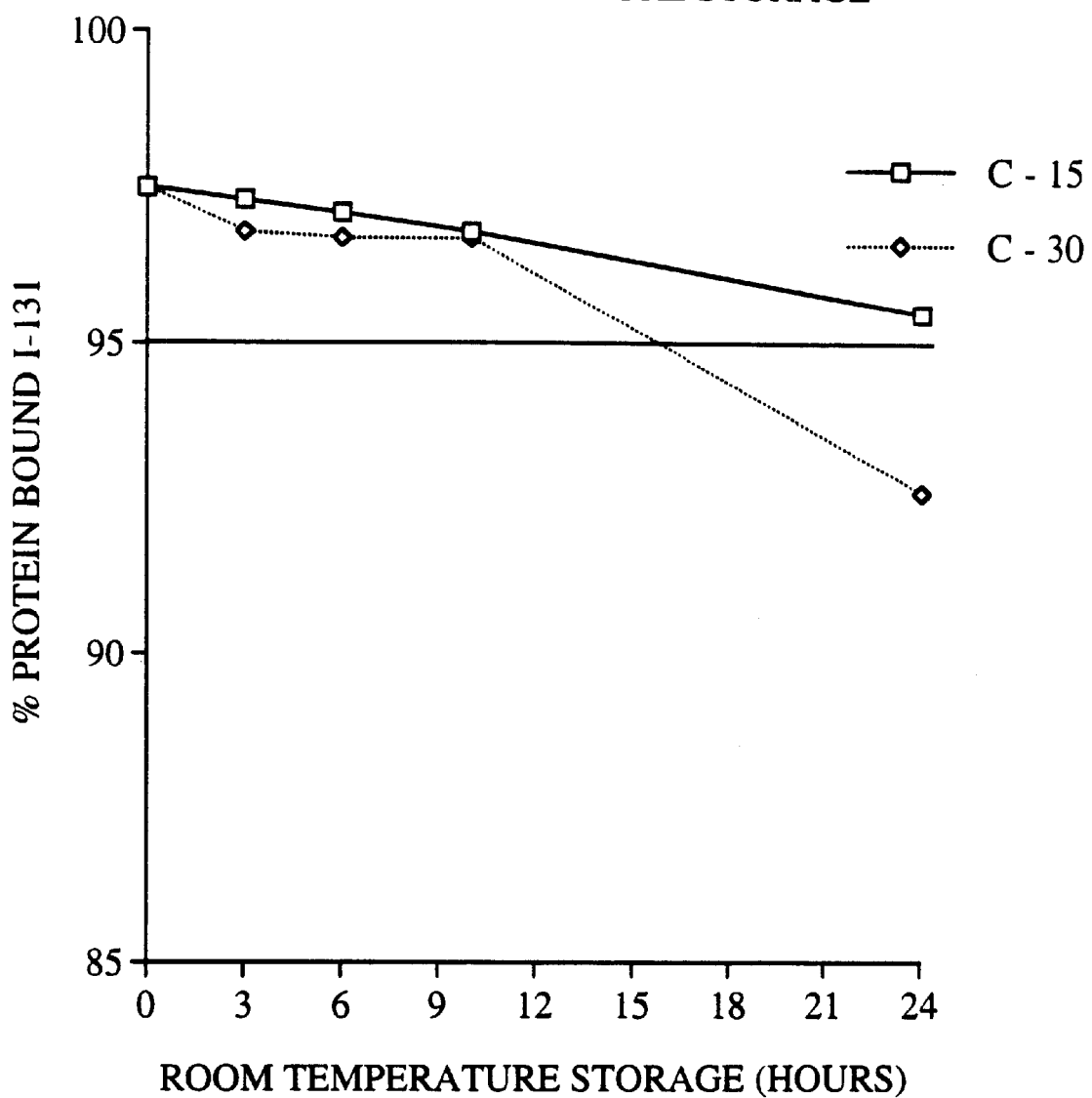

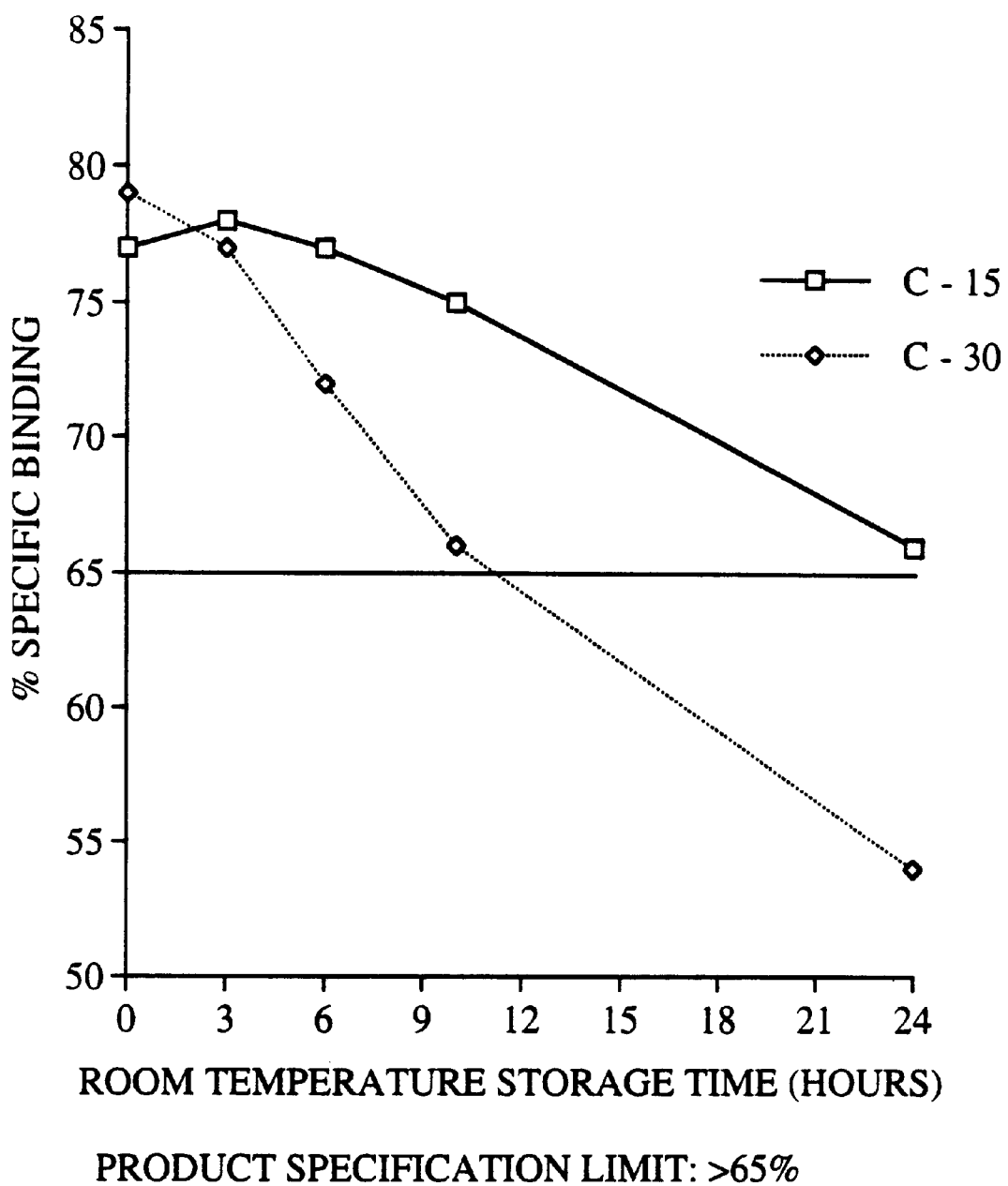

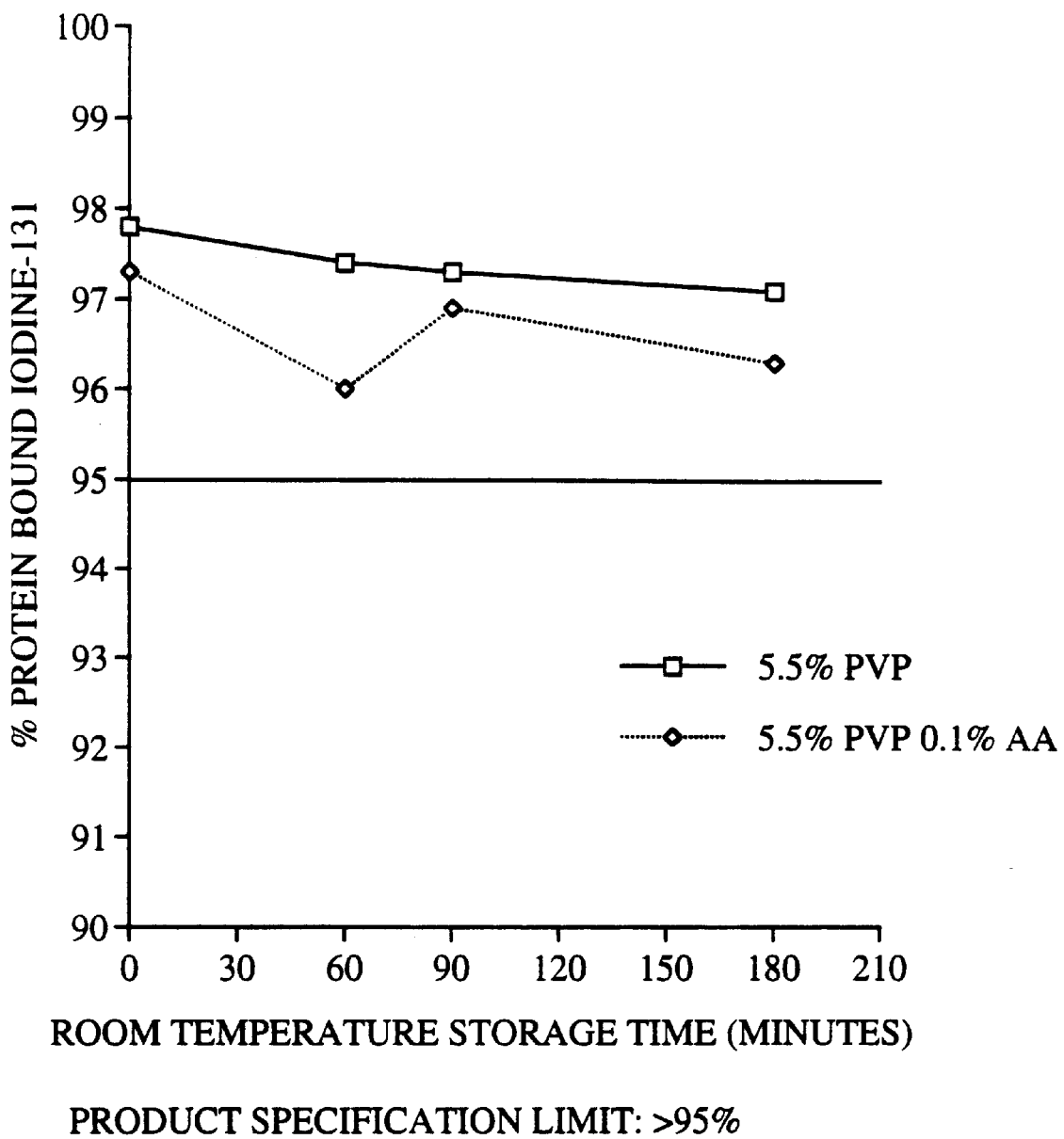

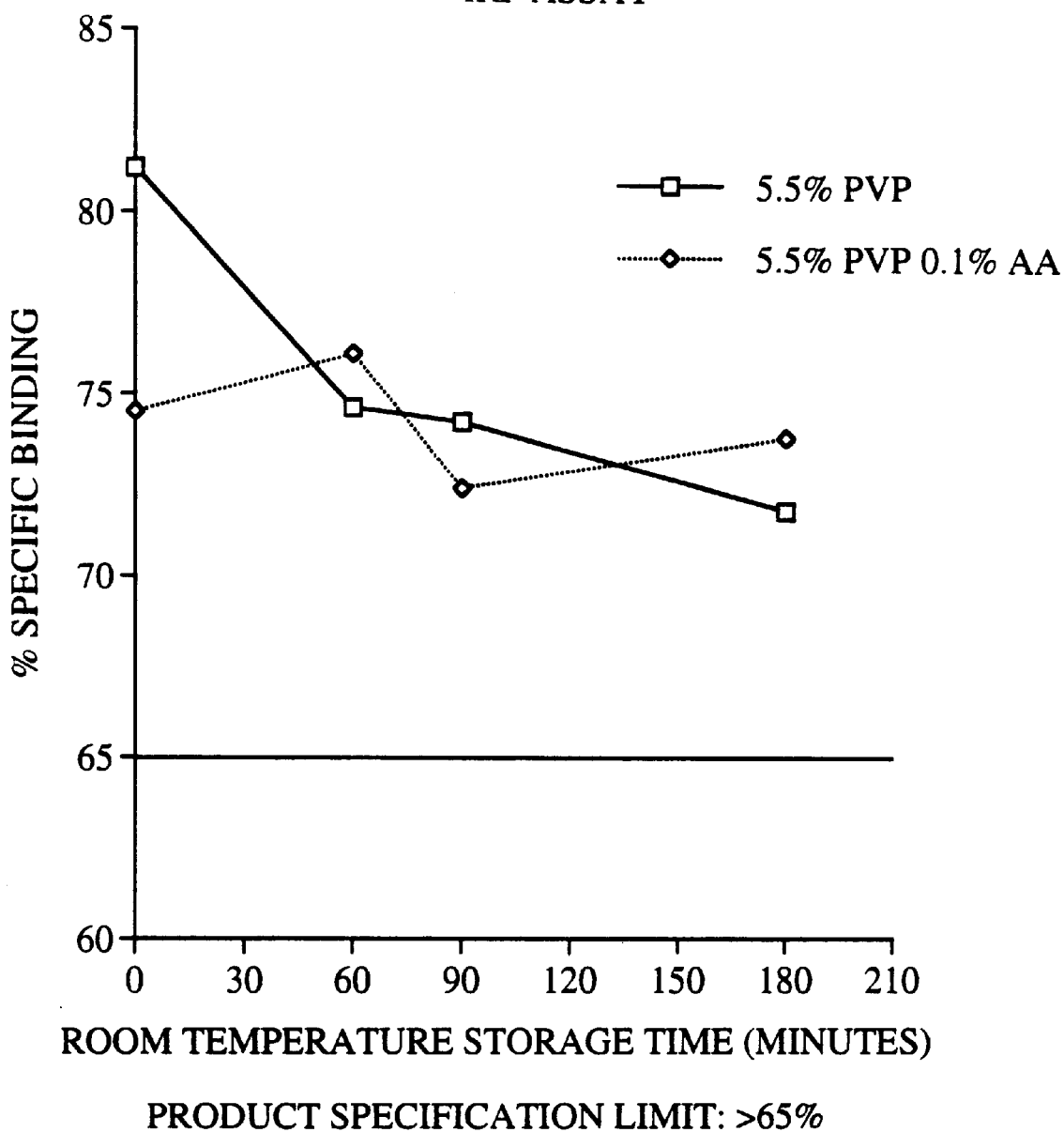

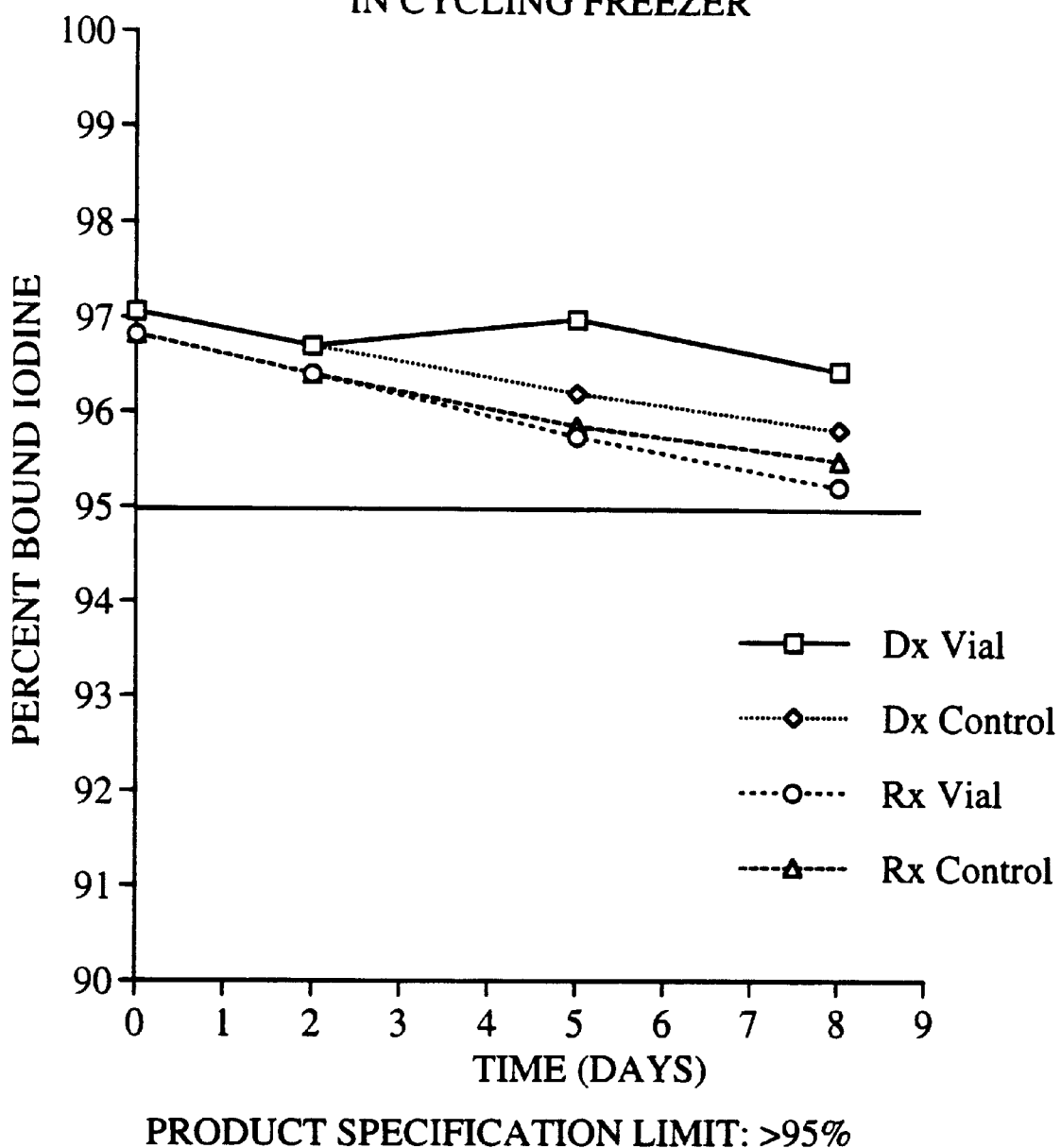

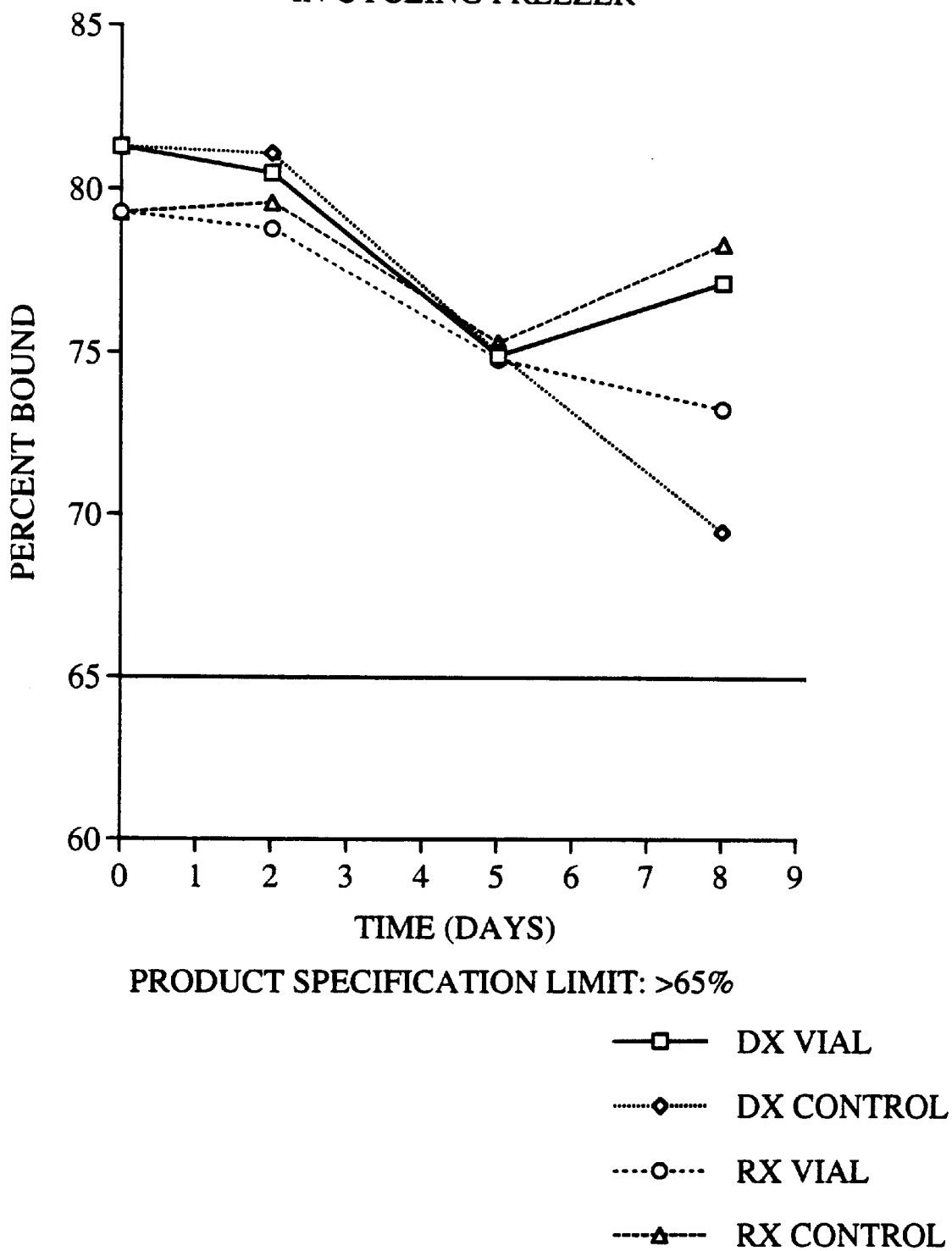

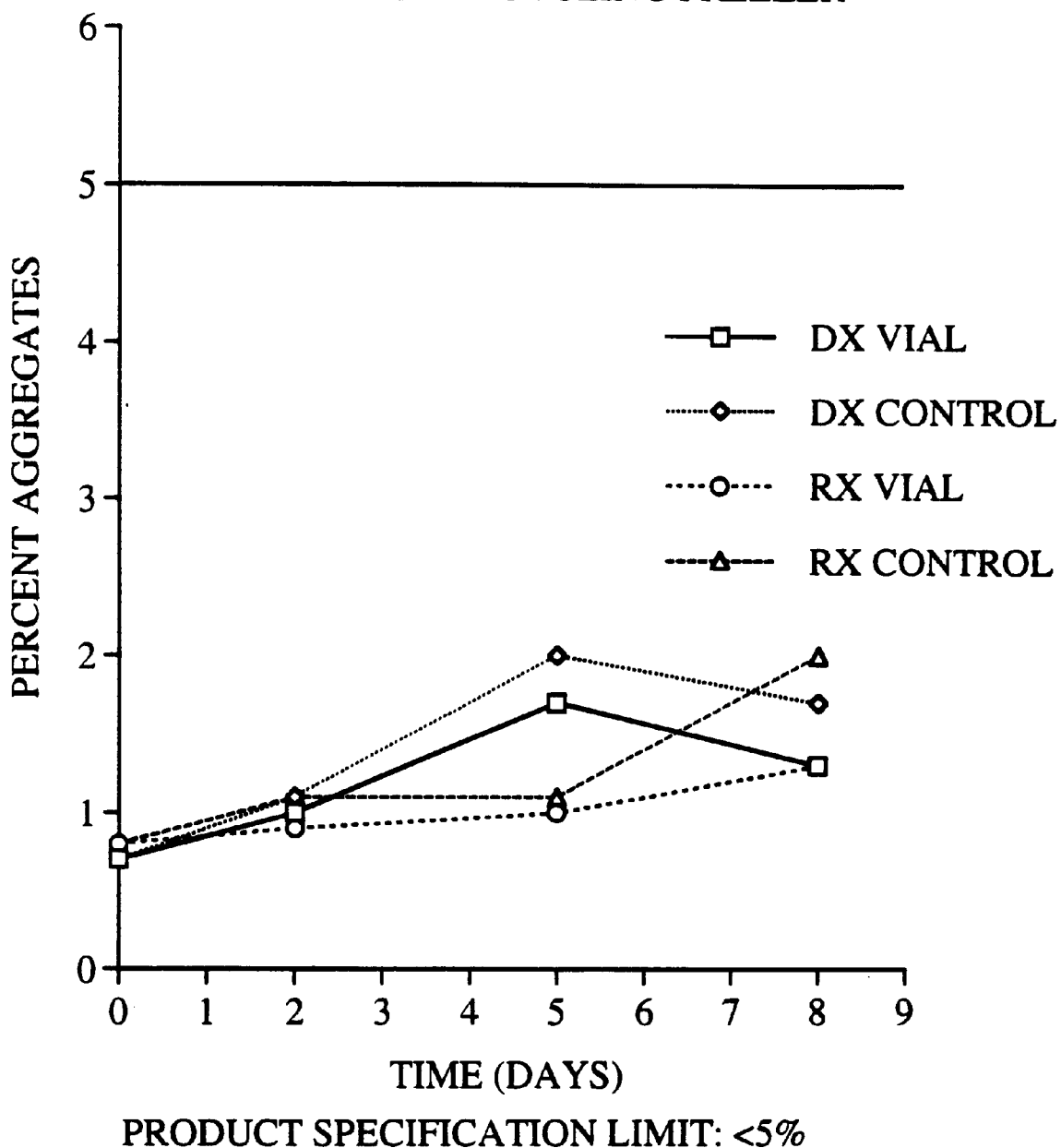

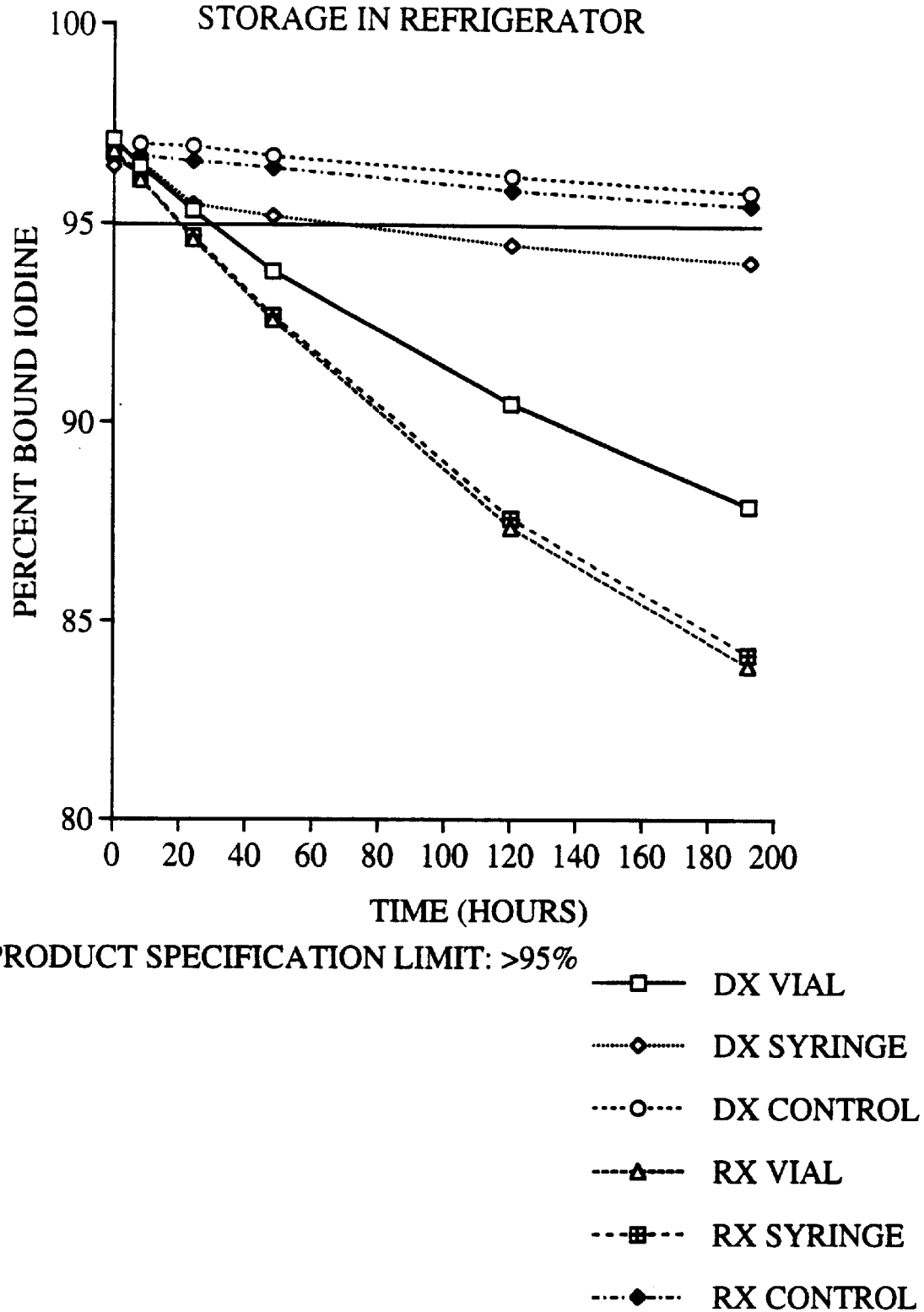

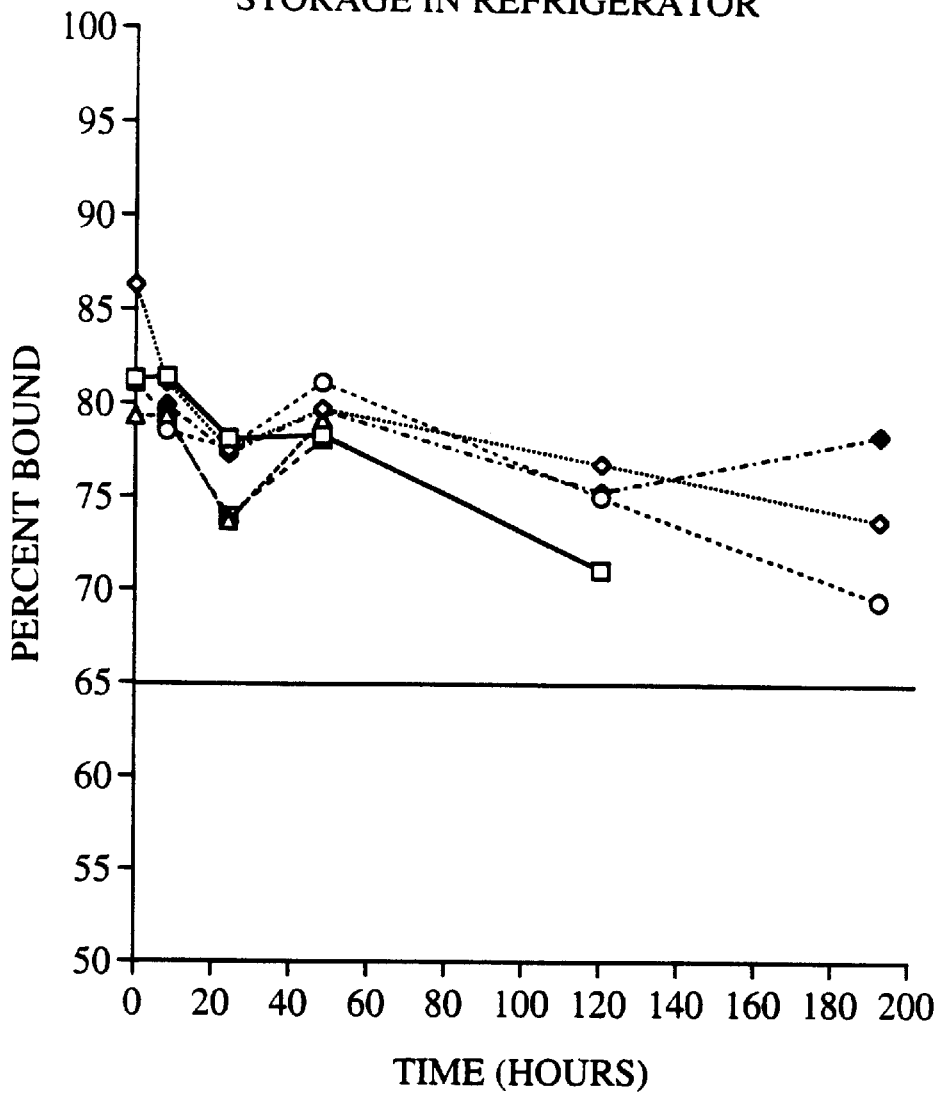

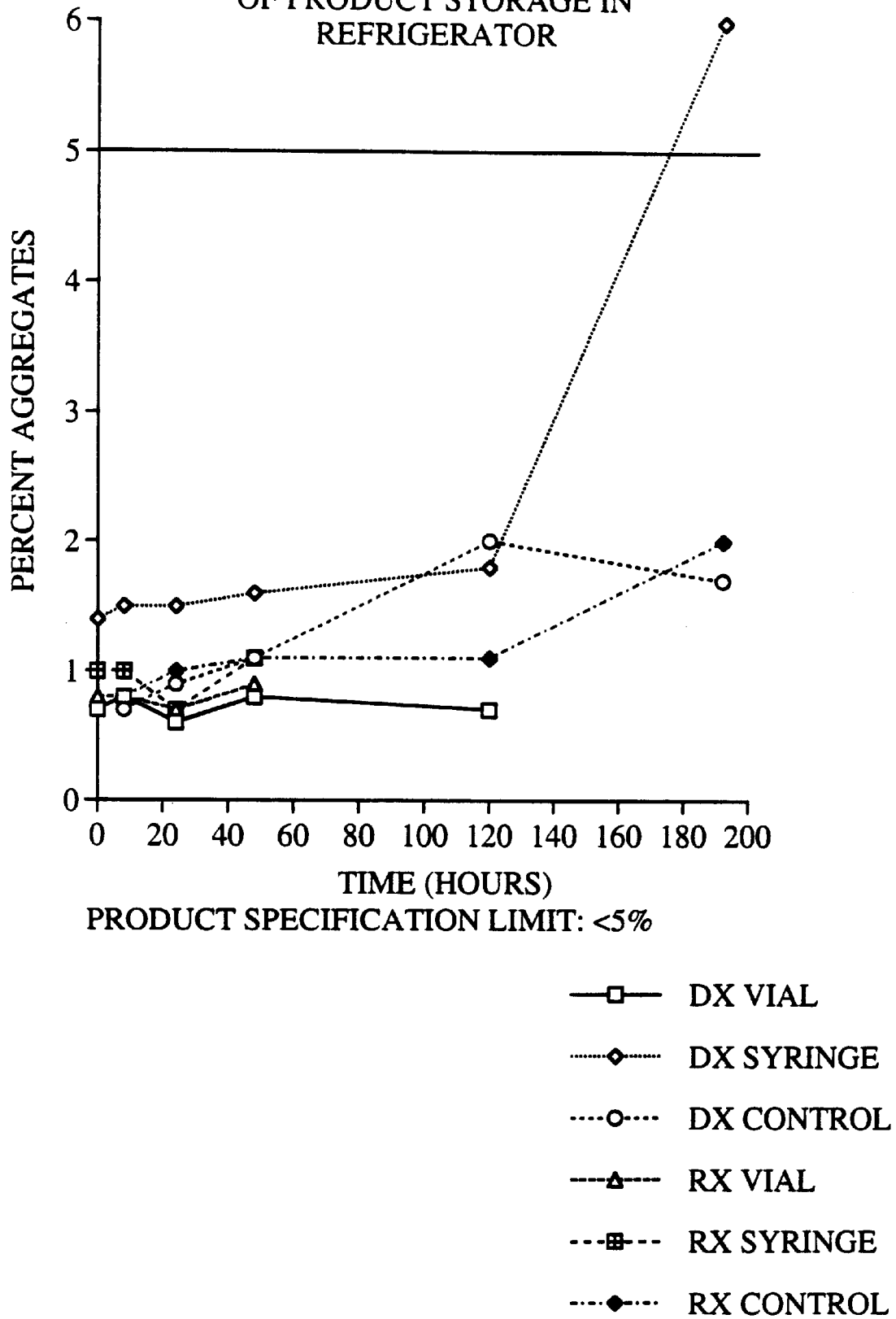

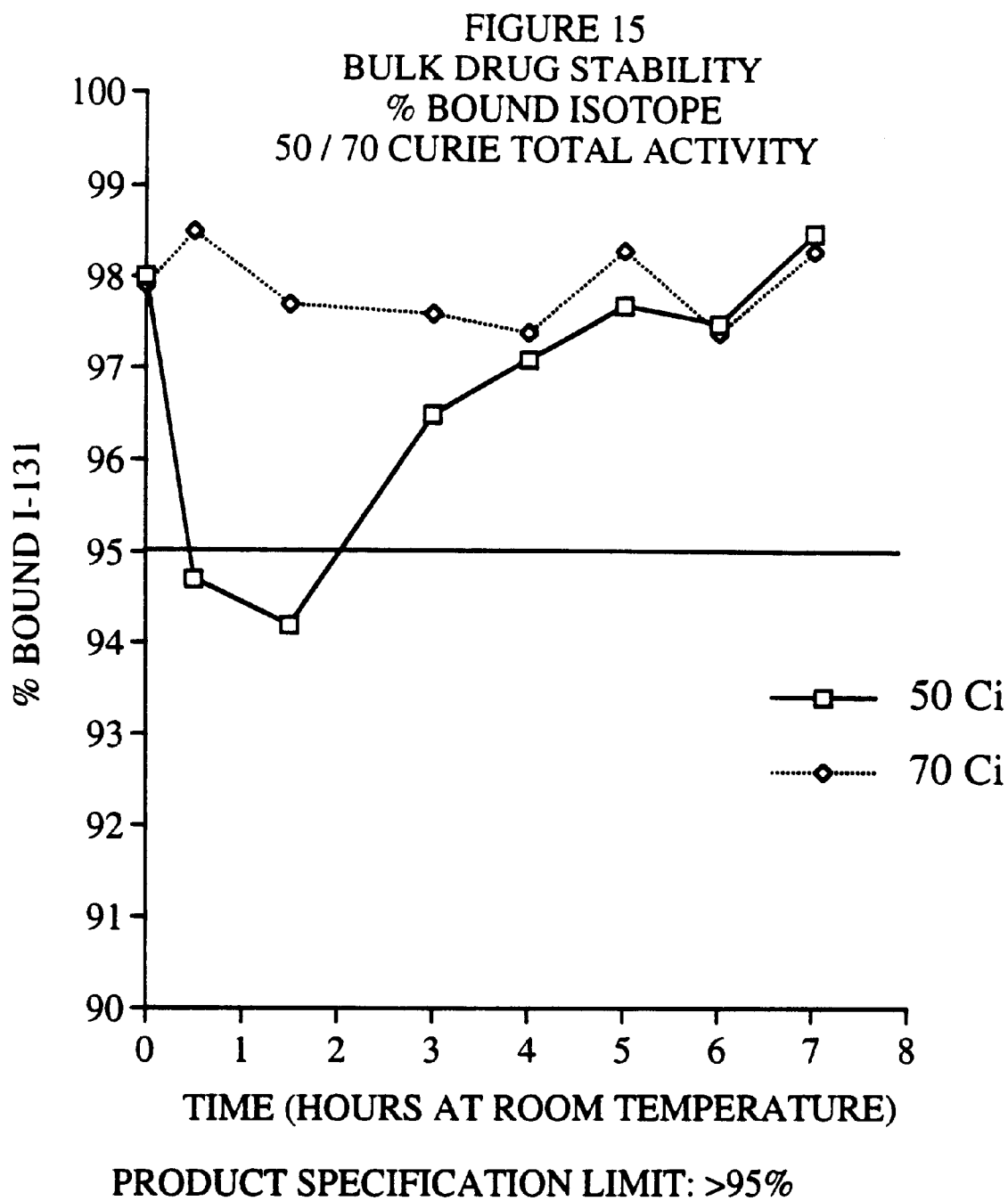

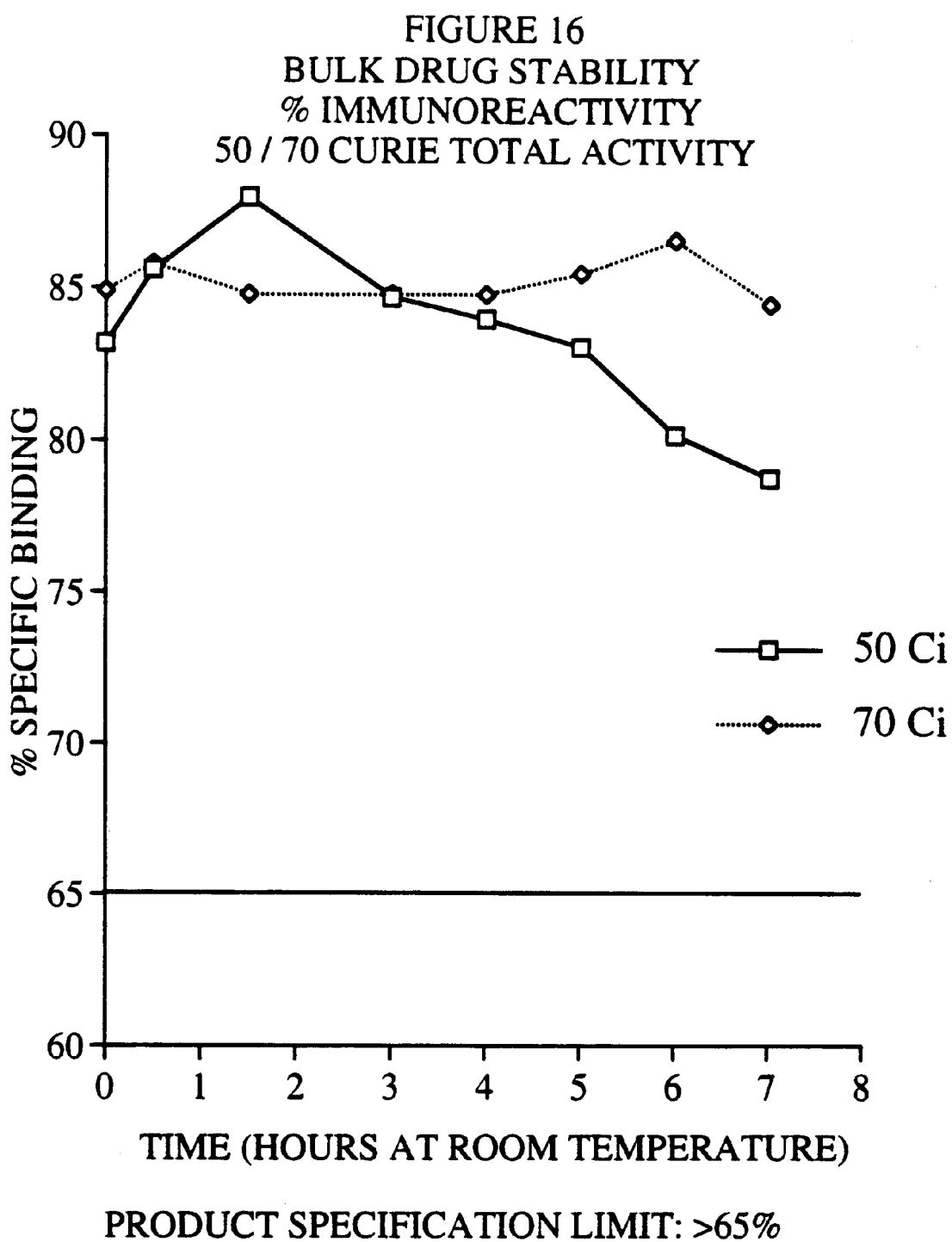

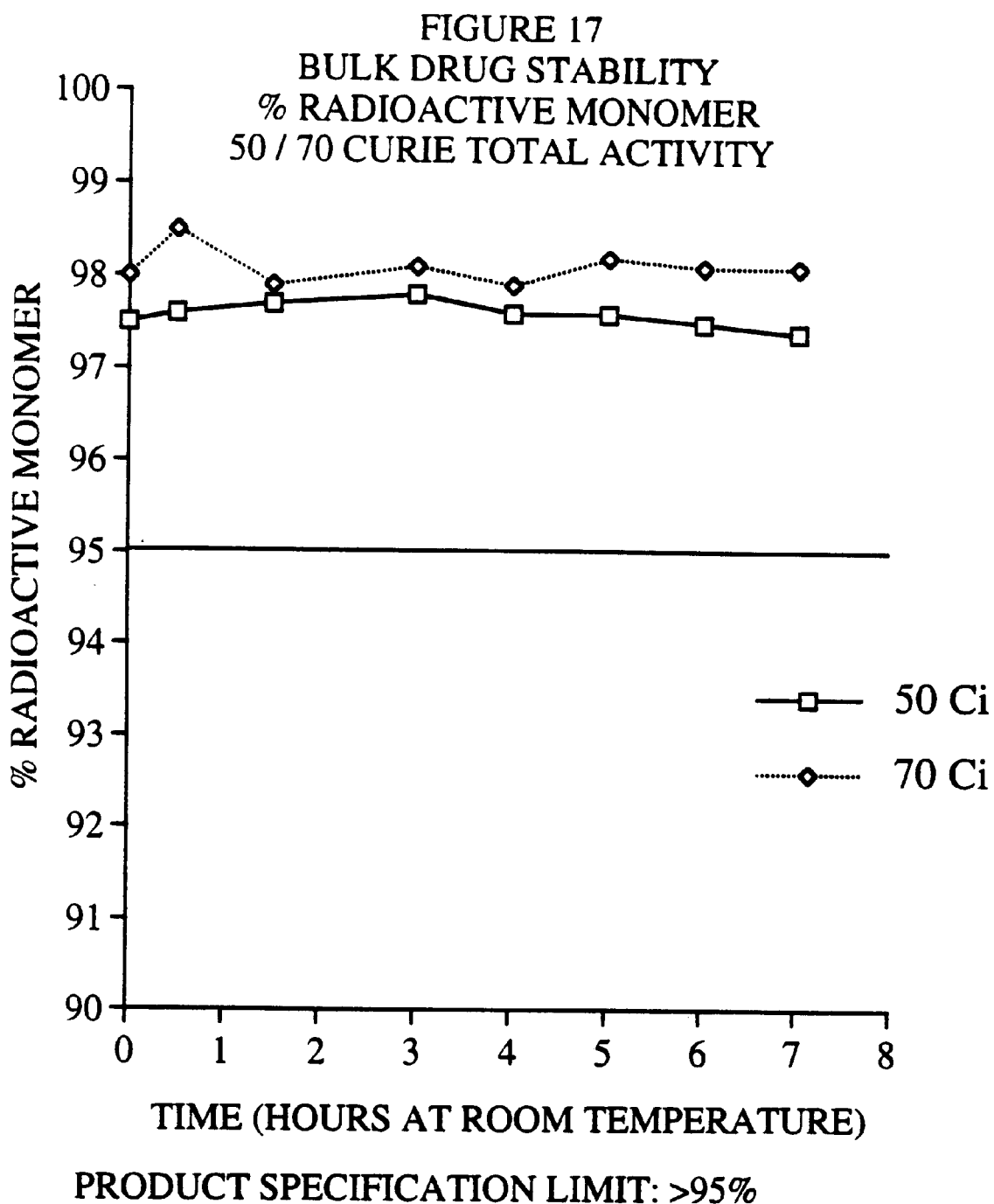

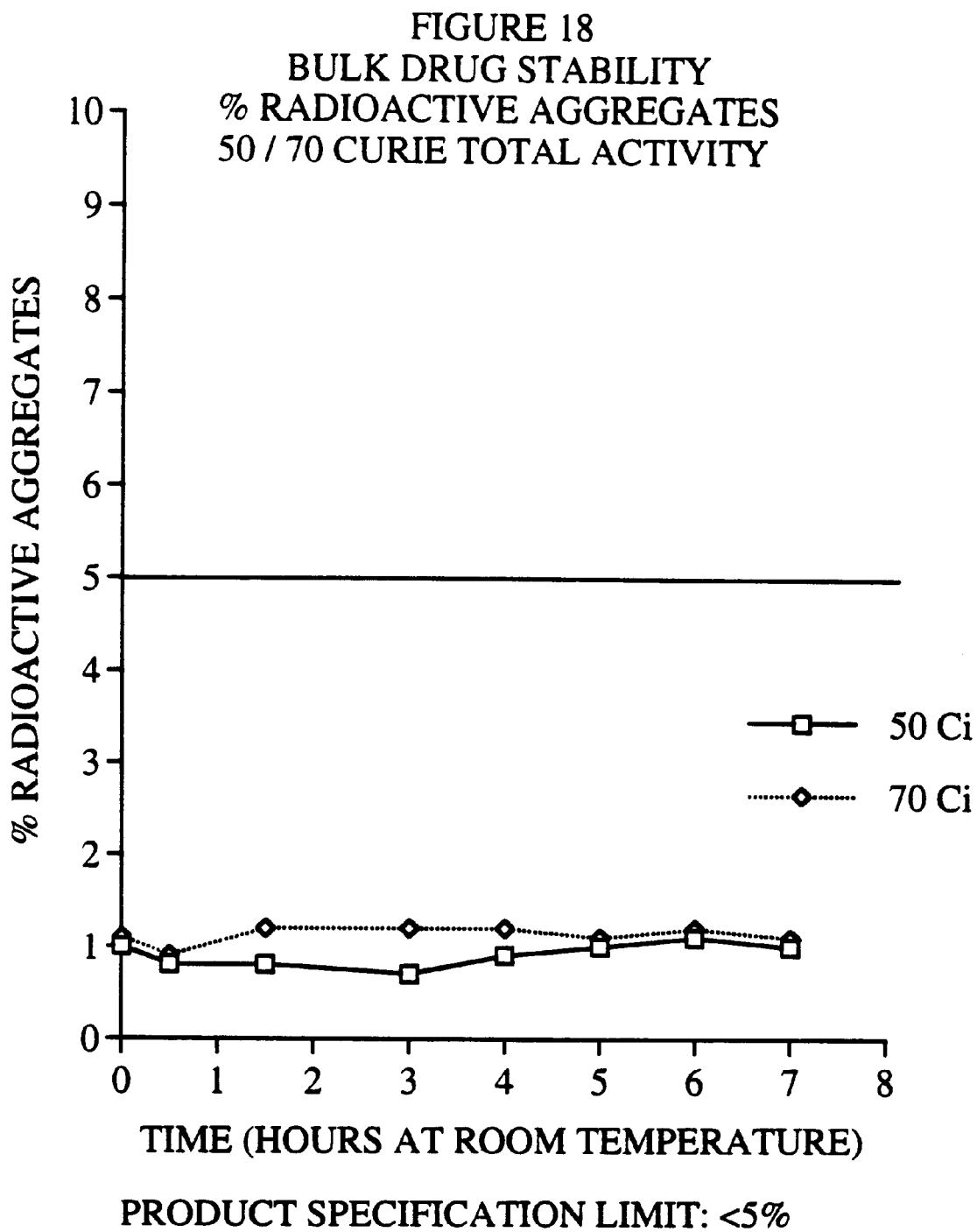

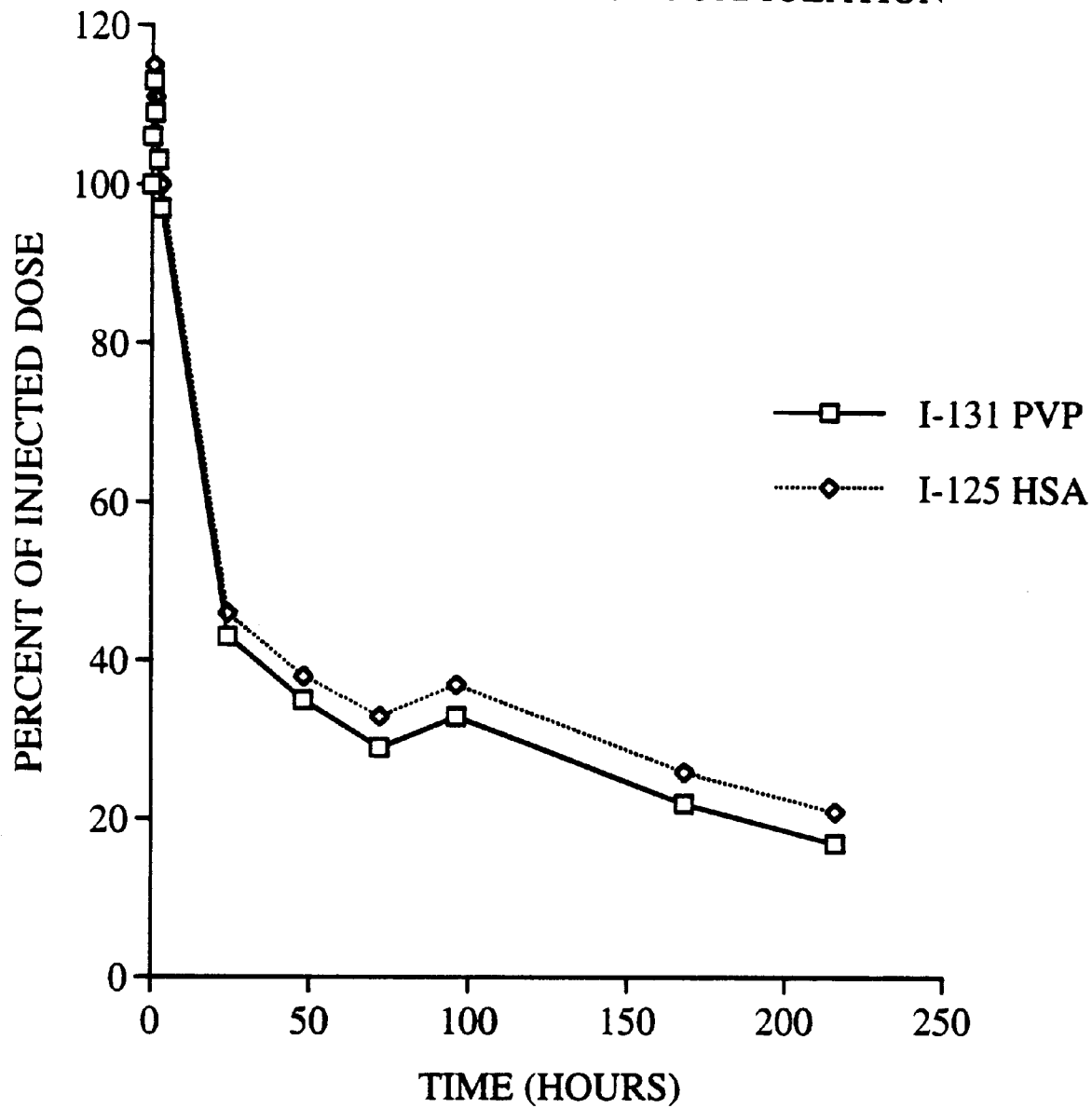

US 6,338,835 B1

RADIOPROTECTANT FOR PEPTIDES LABELED WITH RADIOISOTOPE

CROSS REFERENCE TO RELATED APPLICATIONS

This application is a continuation International Patent Application No. PCT/US98/11428 filed Jun. 3, 1998 and published as WO 98/55154 on Dec. 10, 1998, which claims priority from U.S. provisional Application No. 60/048,387 filed Jun. 3, 1997 and a continuation of U.S. Application Ser. No. 08/918,525 filed Aug. 21, 1997 now U.S. Pat. No. 5,961,955 issued Oct. 5, 1999.

INTRODUCTION

1. Technical Field

This invention relates to the use of protectants for radio-labeled peptides, including antibodies and other proteins as well as small peptides.

2. Background

Radioimmunotherapy and radioimmunodiagnosis deliver critical treatment or imaging agents preferentially to the necessary areas of the body. This focused approach is especially promising because it reduces deleterious side effects. Antibodies, and particularly monoclonal antibodies, are often the critical agents that deliver a payload of radioactivity to tumors or to specific tissue areas within the body of the patient that will benefit most from the therapeutic or diagnostic radioactive emissions. Other peptides are also used in this manner for targeted delivery of radioisotopes through ligand-receptor coupling.

A common problem encountered with radiolabeled antibodies, as well as with other peptides, however, is that the integrity of the radiolabeled product may be short-lived. The radioisotope carried by the peptide contributes to the degradation of the peptide, a process known as autoradiolysis, beginning immediately after the peptide is radiolabeled and often causing unacceptable levels of degradation before the radiolabeled product can be administered to the patient to provide beneficial effect. This has proven to be a particular problem with large peptides, usually referred to as proteins, such as antibodies. Since the structure and conformation of the molecule is relevant to its activity, even a single modification of its original structure can result in deleterious effects on the functionality. For example, sensitive, and sometimes difficult to obtain, proteins or peptides such as monoclonal antibodies may suffer damage caused by the particle emissions of the radioisotopes or by the generation of free radicals in an aqueous environment in the presence of radioisotopes.

The propensity to autoradiolysis has contributed to difficulty with storage and shipping of radiolabeled products and often necessitates that the actual radiolabeling of the product be conducted at the site of patient administration rather than at a central radiolabeling facility. Many radiopharmacies are unable to perform high dose radiolabeling, thus limiting availability to patients. In those radiopharmacies equipped to perform such radiolabeling, specialized training of personnel is required. Furthermore, under these circumstances, the likelihood of reproducible product is reduced and the cost of treatment is substantially increased. The on-site radiolabeling must also generally be performed on the same day as the patient is to be treated.

Human serum albumin (HSA) has been previously used to protect radiolabeled antibodies. The use of HSA in a drug formulation is problematic, however, because of cost, supply difficulties, and most importantly, the potential for contamination with viruses and other pathogens. For instance, commercial supplies of HSA have been recalled due to possible transmission of diseases such as Creutzfeldt-Jakob Disease. Other materials, such as gentisic acid (see U.S. Pat. No. 5,384,113) and propylene glycol, have been proposed as alternatives. However, considerations such as patient acceptance, costs, and incompatibility with drugs administered for other purposes continually call for alternatives to existing radioprotectants. Accordingly, there is a need for additional materials and techniques for the radioprotection of peptides.

SUMMARY OF THE INVENTION

Accordingly, it is an object of the invention to provide a method and composition for the radioprotection of peptides using a material of different structure and activities than those previously used for this purpose.

The above object has been met by the use of povidone, also widely known as polyvinylpyrrolidone or PVP, as a radioprotectant to ameliorate the degradation of radiolabeled peptides, especially radiolabeled proteins such as antibodies. The povidone may be used alone or in combination with ascorbic acid or another secondary stabilizer as a radioprotectant.

Another aspect of the invention is a stable peptide-radioisotope composition comprising a radiolabeled peptide protected by either povidone alone or povidone in combination with ascorbic acid or another secondary stabilizer.

A further aspect of the invention is a method for making a stable peptide-radioisotope composition by labeling the peptide with a radioisotope and then contacting the radiolabeled peptide with a povidone radioprotectant.

An article of manufacture wherein a radioprotectant is provided together with instructions for its use to ameliorate the degradation of radiolabeled peptides is also included.

BRIEF DESCRIPTION OF THE DRAWINGS

FIG. 3 is a graph showing ITLC analysis of different concentrations of povidone.

FIG. 4 is a graph showing 5% povidone as a radioprotectant at room temperature and frozen storage.

FIG. 5 is a graph showing stability of a radiolabeled product containing different molecular weight forms of povidone at room temperature storage.

FIG. 6 is a graph showing potency of a radiolabeled product containing different molecular weight forms of povidone at room temperature storage.

FIG. 7 is a graph showing ITLC analysis of povidone and povidone/ascorbic acid radioprotectants in bulk drug products at room temperature storage.

FIG. 8 is a graph showing IRF analysis of povidone and povidone/ascorbic acid radioprotectants in bulk drug products at room temperature storage.

FIG. 9 is a graph showing ITLC analysis of a radiolabeled product under cycling freezer conditions.

FIG. 10 is a graph showing IRF analysis of a radiolabeled product under cycling freezer conditions.

FIG. 11 is a graph showing percentage aggregation of a radiolabeled product under cycling freezer conditions.

FIG. 12 is a graph showing ITLC analysis of a radiolabeled product under refrigerator storage conditions.

FIG. 13 is a graph showing IRF analysis of a radiolabeled product under refrigerator storage conditions.

FIG. 14 is a graph showing percentage aggregation of a radiolabeled product under refrigerator storage conditions.

FIG. 15 is a graph showing ITLC analysis of a radiolabeled product in high level radioactive fields.

FIG. 16 is a graph showing percentage immunoreactivity of a radiolabeled product in high level radioactive fields.

FIG. 17 is a graph showing the percentage of radioactive monomers for a radiolabeled product in high level radioactive fields.

FIG. 18 is a graph showing percentage aggregation of a radiolabeled product in high level radioactive fields.

FIG. 19 is a graph showing the blood clearance profile for a typical composition of the invention vs. an HSA formulation.

DESCRIPTION OF SPECIFIC EMBODIMENTS

Figure 1:
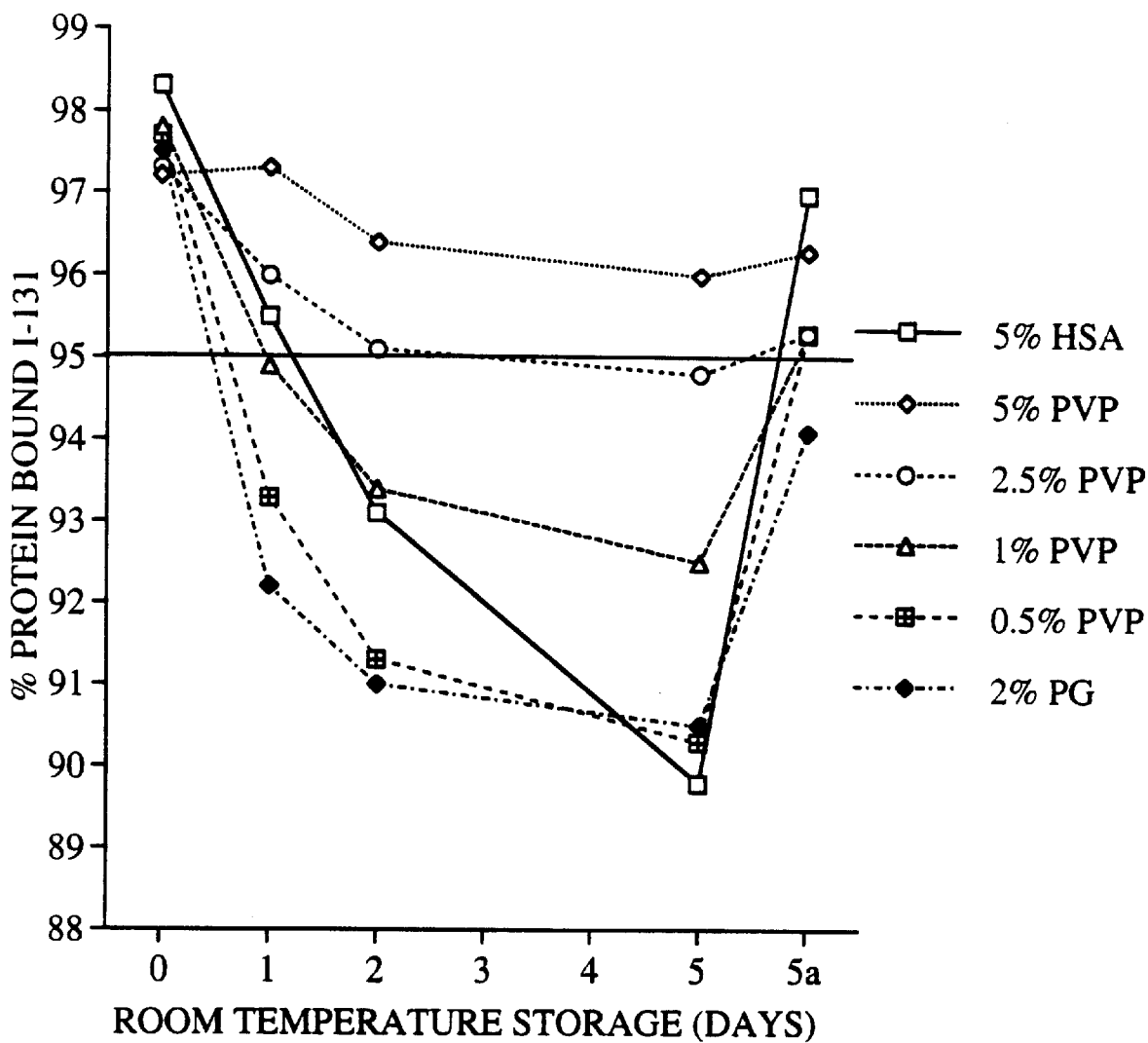
FIG. 1 is a graph showing different percentages of povidone as a radioprotectant at room temperature storage.

Povidone is a synthetic polymer consisting essentially of linearly polymerized 1-vinyl-2-pyrrolidinone (vinylpyrrolidone), the degree of polymerization of which results in polymers of various molecular weights. Povidone is a well-known material and is commercially available in a variety of grades, including pharmaceutical grade. For a detailed description of U.S. pharmaceutical (USP) grade povidone, see, for example, various publications of commercial suppliers, such as the. product literature for Plasdone® C-15/Plasdone® C-30/Povidone USP available from GAF Chemicals Corporation, 1361 Alps Road, Wayne, N.J.

Povidone is typically characterized by its viscosity in aqueous solution, relative to that of water, expressed as a K-value, typically ranging from 10 to 120. A K-value is a function of molecular weight as indicated by viscosity measurements and is calculated using Fikentscher's equation; see Fikentscher et al., Modem Plastics, 23(3):157–161, 212, 214, 216, 218 (1945). Povidone having a K-value of 17 has an approximate viscosity average molecular weight (Mv) of 7 kD and an approximate weight average molecular weight (Mw) of 10 kD. Povidone having a K-value of 30 has an approximate viscosity average molecular weight of 38 kD and an approximate weight average molecular weight of 50 kD.

Povidone has been used in pharmaceutical formulations for many years, being first used in the 1940s as a plasma expander, although it has now been superseded for this purpose by dextran. Povidone is also widely used as an excipient, particularly in oral tablets and solutions, and is regarded as essentially nontoxic. Povidone additionally is used topically and has no irritant effect on the skin and causes no sensitization.

As povidone forms a network-like structure when mixed with water and the resulting material has increasing viscosity with an increase in the percent by weight povidone in the mixture, the amount of povidone present in a particular formulation as a radioprotectant can be adjusted to provide varying degrees of protection and viscosity, depending on the needs of the particular formulation. Generally, upper limits on the amount of povidone present are determined by the desired or required viscosity of the formulation. For example, injectable and intravenous (IV) formulations will generally contain less than 20% povidone (all percentages herein are by weight per volume of the overall formulation unless otherwise stated), more usually less than 10%, preferably less than 7.5%. The most preferred injectable and IV formulations contain 5–6% povidone. Higher concentrations may be used for other purposes that are not limited by viscosity, as radioprotection continues to exist in higher concentrations. Lower limits on the povidone present in a composition are determined by the desired amount of radioprotection, which will vary with the radioactivity of the formulation, usually measured in millicuries (mCi). The invention is preferably used with peptide-radioisotope compositions having an activity concentration of 7.5 mCi/ml or less. Povidone has been found to provide excellent protection, however, of a test antibody labeled with $^{131}$I at an activity concentration as high as 10 mCi/ml when present at a concentration of 5% of the formulation and, of course, provides statistically significant protection even when present in much lower amounts.

According to the invention, povidone is provided in a formulation in a minimum amount sufficient to ameliorate degradation of the peptide by radioactivity, usually measured by a decrease in biological activity of the peptide (such as ability of an antibody or other peptide to bind to a specific antigen or substrate) or the level of peptide-bound radioactivity over time, to produce a stable peptide-radioisotope composition. As used herein, the term "stable" means maintaining biological activity and physicochemical integrity above a level considered generally acceptable for the intended use of the peptide. For example, a stable peptide-radioisotope composition of the invention will maintain the biological activity and physicochemical integrity necessary for administration to a patient for therapy or diagnosis over the time period necessary for the administration. Furthermore, stable peptide-radioisotope compositions include compositions that have potency at or above 55% specific binding as measured, e.g., by immunoreactive fraction (IRF) assay or stability at or above 90% peptide-bound radioactivity as measured, e.g., by instant thin layer chromatography (ITLC). Of course, peptides that are intended for use in human therapy may call for higher levels of biological activity and physicochemical integrity than do peptides to be used, e.g., in in vitro diagnostic kits. The stable peptide-radioisotope compositions of the invention preferably have povidone present in a range of about 0.5–10% (w/v) of the composition, more preferably 1–7.5% (w/v) of the composition, and even more preferably 5–6% (w/w) of the composition.

There are no particular limitations on the molecular weight of the povidone used as a radioprotectant, as povidones of all tested molecular weights have provided statistically significant radioprotection. Accordingly, povidones having a K-value within the range of K-17 to K-30 are suitable for use in the invention, i.e., povidones with a viscosity average molecular weight within the range of about 6–38 kD and a weight average molecular weight within the range of about 10–50 kD. However, povidone with a viscosity average molecular weight of 6–8 kD and a K-value of K-17 is preferred as it has proven to be somewhat more radioprotective over longer time periods than an equal amount of povidone having a higher viscosity average molecular weight.

While povidone can provide sufficient radioprotection by itself, it is of course possible to combine povidone with other materials for additional protection or for other purposes. For example, ascorbic acid is commonly used to prevent deleterious oxidation of proteins and can be used for that purpose in a formulation containing povidone. Ascorbic acid, also known as vitamin C, is a readily available GRAS (generally recognized as safe) substance often used in pharmaceutical compositions and other formulations used for biological purposes and may be used at levels as high as 10mg/ml of the final formulation but the lowest effective concentration, generally in the range of 0.9–1.3 mg/ml, is preferred. A combination of 5–6% w/v povidone with 1 mg/ml (0.1% w/v) ascorbic acid was particularly useful in some of the formulations discussed in the examples below. Other examples of secondary stabilizers that can be used in compositions of the invention to supplement povidone's radioprotective ability include benzyl alcohol, cysteamine, cystamine, propylene glycol, dextran, and gentisic acid.

Secondary stabilizers such as ascorbic acid are especially useful in combination with povidone for radioprotection of certain radiolabeled peptide compositions. For example, a radiolabeled peptide that needs to be produced in large quantity for therapy purposes may be collected in a large vessel or container. There is a high level of radioactivity contained in the bulk formulation in comparison to the level present in a vial of the radiolabeled peptide. When working in bulk, the deposition of γ energy from photons is much higher than in a small volume, i.e. there is increased deposition, and thus greater potential for damage to the peptide, per unit volume. Greater radioprotection may therefore be needed. An increase in the povidone concentration in this instance may not be desirable due to the increased viscosity of the final radiolabeled peptide composition that such an increase would provide. Therefore, ascorbic acid or another secondary stabilizer may be combined with the povidone to provide increased radioprotection without a concomitant increase in viscosity depending upon the specifics of production and the desired final characteristics of the radiolabeled peptide composition. Ascorbic acid has been especially useful in combination with povidone in protecting a large-scale production of a radiolabeled peptide composition against damage by the photon emission of a radioisotope in some of the examples presented below. Secondary stabilizers are preferentially utilized in combination with povidone for radioprotection when the radiolabeled peptide provides radioactive fields greater than 600 mCi and activity concentration values of greater than 5 mCi/ml. Improved stability with the addition of secondary stabilizers has also been shown for radiolabeled peptides having radioactive fields as high as 50 Ci and 70 Ci, with an activity concentration value of 8.2 mCi/ml.

The invention thus includes a stable peptide-radioisotope composition having a radiolabeled peptide and povidone as a radioprotectant. The stable composition is shielded against autoradiolysis to a significant degree. Additionally, the composition may include ascorbic acid or another secondary stabilizer in combination with the povidone to serve as the radioprotectant.

Another aspect of the invention is a method for ameliorating degradation of a composition that includes a radiolabeled peptide wherein a radioprotectant comprising povidone, or povidone in combination with ascorbic acid or another secondary stabilizer, is added to the radiolabeled peptide composition. The invention also includes a method for making a stable peptide-radioisotope composition wherein the peptide is radiolabeled by a known method and then contacted with a radioprotectant of the invention. Ideally, the radioprotectant should be contacted with the radiolabeled peptide immediately after the peptide is radiolabeled. For instance, in a process for creating radiolabeled peptides, whether conducted in a relatively small-scale clinical setting or as part of a larger scale manufacturing production, the peptide may be radiolabeled and collected directly into an appropriate container having the radioprotectant to minimize the time the radiolabeled peptide is likely to suffer autoradiolysis.

A further aspect of the invention is a radioprotectant, or stabilizer, comprising povidone, or povidone in a stabilizer solution (for example an elution buffer) or in combination with ascorbic acid or another secondary stabilizer, in concentrations generally useful for radioprotection of radiolabeled peptides or customized to a particular peptide and a particular radioisotope. The radioprotectant is preferably provided as a stabilizer solution that can be combined with the prepared radiolabeled peptides as by adding the stabilizer solution directly to the radiolabeled peptides.

The invention further includes an article of manufacture comprising the radioprotectant of the invention in combination with instructions for using the radioprotectant to ameliorate degradation of a radiolabeled peptide by radioactivity.

Radiolabeling of peptides (which is not itself part of the present invention) can be achieved using various methods known in the art. For example, peptides can be labeled with a radioactive isotope through use of a chelating agent or by covalent labeling with a material capable of direct reaction with a peptide (such as iodine), as well as by direct labeling (substitution of a radioactive isotope, such as $^{14}C$ or tritium, for an atom present in the peptide). See U.S. Pat. No. 5,384,113, as well as numerous other patent and other publications, for general techniques available for the radiolabeling process (as well as other general information relating to preparation of formulations containing radioisotopes other than protection using povidone as described herein). As used herein, the term "radiolabeled" describes a product that has been attached to a radioisotope by any of the various known methods, such as by covalent labeling or covalent binding, by a direct substitution method, or by a chelation method, and also describes a peptide that is in close association or proximity to a radioisotope as in a physical mixture. Mixtures of peptides and radioisotopes will also benefit from the radioprotectant of the invention. By extension, the terms "peptide-bound" or "protein-bound," as in peptide-bound radioactivity or protein-bound $^{131}I$ values, also refer to such mixtures, as does the term "peptide-radioisotope composition."

The invention may be used widely for peptides of various sizes and conformations. The term "peptide" as used herein thus includes small peptides, large polypeptides, and proteins of all ranges of complexity. Similarly, the invention is not limited by the type of radioisotope present in the radiolabeled peptide composition. The radioprotectant provides protection to the peptide from radioisotopes that emit βparticles, photons (x-rays and γ emissions), α particles, Auger electrons, and/or internal conversion electrons. Thus, the invention may be advantageously used to protect peptides against autoradiolysis resulting from a broad range of radioisotopes including $^{111}In$, $^{67}Ga$, $^{90}Y$, $^{131}I$, $^{125}I$, $^{123}I$, $^{32}P$, $^{47}Sc$, $^{67}CU$, $^{109}Pd$, $^{111}Ag$, $^{153}Sm$, $^{166}Ho$, $^{177}Lu$, $^{186}Re$, $^{188}Re$, $^{199}Au$, $^{211}At$, $^{212}Bi$, $^{223}Ra$, $^{225}Ac$, $^{213}Bi$, and $^{99m}Tc$.

Testing of the integrity of radiolabeled product can be carried out, e.g. by measuring immunoreactivity to determine the functionality of a radiolabeled antibody over time or by using thin layer chromatography, e.g. by instant thin layer chromatography (ITLC), to measure unbound iodine or other radioisotope values or to determine the separation of a radioisotope from a chelating agent. High Pressure Liquid Chromatography (HPLC) may also be performed to check for undesirable aggregation, fragmentation, or release of unbound radioisotope.

Improved stability over time for compositions of the invention can be demonstrated by determining stabilized biological activity and/or radioisotope attachment (for example, immunoreactivity and bound iodine or other radioisotope values) in samples taken at representative timepoints. The formulations of the invention are effective in maintaining the long-term stability of samples that have been frozen, thawed, and retested up to and including 8 days post-production. Samples maintained at ambient temperatures up to and including 8 hours post-production have also remained stable.

The invention now being generally described, the same can be understood by reference to the following detailed examples of the invention, which are provided for purposes of illustration only and are not to be considered limiting of the invention unless so specified. Most of these examples are directed to use of $^{131}$I-labeled anti-CD20 antibody to treat patients as described in U.S. Pat. No. 5,595,721.

EXAMPLES 1

FORMULATIONS OF $^{131}$I-LABELED ANTI-CD20 ANTIBODY WITH RADIOPROTECTANT

Formulations of radiolabeled product have been prepared according to the present invention for use in the radioimmunotherapeutic treatment that is described in U.S. Pat. No. 5,595,721. Specifically, $^{131}$I-labeled B1 antibody, which is a monoclonal antibody directed against CD20 antigen, is part of a composition having the radioprotectant of the present invention. Additionally, the composition contains well-known physiological buffers and stabilizers, such as potassium phosphate, sodium chloride, and maltose.

For the described formulations, the povidone is generally prepared from povidone powder in an elution buffer (containing potassium phosphate and sodium chloride) to make a concentrated aqueous solution of 22.2% w/v povidone. The pH is adjusted to 7.1±0.1. The solution is aseptically filtered through a 0.22 μm filter and is dispensed into glass bottles. The povidone solution is tested for appearance, concentration, sterility, pH, and endotoxin.

A stock ascorbic acid solution of 11 mg/ml is prepared for these formulations using the elution buffer and ascorbic acid powder. The pH is adjusted to 7.1±0.1. The solution is then aseptically filtered through a 0.22 μm filter and is dispensed into glass bottles. The stock ascorbic acid solution is tested for appearance, concentration, pH, bioburden and endotoxin.

Formulations for treatment of Non-Hodgkin's Lymphoma are prepared by a central radiolabeling site and shipped to a clinical site. The formulations are stable throughout normal shipment and administration schedules for the therapy described. Pharmaceutical formulations containing antibody in either a trace-labeled dose (for imaging or dosimetry studies) or a therapeutic dose (for radioimmunotherapeutic treatment of the patient) can be made by a central facility, stored, and shipped to clinical treatment sites using the radioprotecting formulations of the invention. The invention has made central-site radiolabeling a practicality.

A dosimetric vial typically contains 1.4 ml of solution in a 10 ml vial consisting of
Protein concentration: 2.0±0.5 mg/ml
Calibrated activity: 8–12 mCi
Povidone: 5.51±0.5%
Ascorbic Acid: 1.1±0.2 mg/ml
Potassium Phosphate: 12.5 mM (1.23±0.12 mg/ml), pH 7.0–7.2
Sodium Chloride: 150 mM (9.0±0.05 mg/ml)
Maltose: 1–2% (0.01–0.02 g/ml)

A therapeutic vial typically contains 20.0 ml of solution in a 30 ml vial consisting of:
Protein concentration: 2.0±0.5 mg/ml
Calibrated activity: 112–166 mCi
Povidone: 5.5±0.5%
Ascorbic Acid: 1.1±0.2 mg/ml
Potassium Phosphate: 12.5 mM (1.23±0.12 mg/ml), pH 7.0–7.2
Sodium Chloride: 150 mM (9.0±0.05 mg/ml)
Maltose: 1–2% (0.01–0.02 g/ml)

EXAMPLE 2

RELATIVE STABILITY OF RADIOLABELED PRODUCT IN THE PRESENCE OF DIFFERENT POVIDONE CONCENTRATIONS

Samples of $^{131}$I-labeled B1 antibody were prepared with different concentrations of povidone. Particularly, samples were prepared with 0.5%, 1%, 2.5%, and 5% w/v povidone in the final composition. The samples were at an activity concentration of 5 mCi/ml, a specific activity of 3.2 mCi/mg, and an antibody protein concentration of 1.6 mg/ml. Since concentrations of 5–6% povidone have previously been deemed acceptable for physiological administration and the lowest possible effective concentration is generally desirable, higher concentrations of povidone were not tested in this experiment. Samples having a standard concentration (5% w/v) of HSA used for stabilization of radiolabeled products were also prepared, as were samples with a standard concentration (2% w/v) of propylene glycol (PG) used for such stabilization.

The samples were stored at room temperature and tested at Days 1, 2, and 5 for radiochemical purity, or stability of the radiolabeled product, by instant thin layer chromatography (ITLC). A duplicate sample was frozen at −70° C. on Day 0. then thawed and tested at Day 5 for comparison.

The ITLC is performed by applying the sample to the bottom of an ITLC Silica Gel (SG) fiber strip. The thin layer strip is allowed to run in an ITLC chamber in an 80–85% methanol and 15–20% H$_2$O solution. Small molecular weight fragments and unbound iodine will migrate farther from the origin than intact $^{131}$I-labeled B1 antibody. The unbound iodine and small molecular weight fragments are localized in the top half while the intact antibody will remain at the bottom of the strip near the origin. The developed strip is cut in half and each half is measured in a gamma well counter. The radiochemical purity is determined by comparing the cpm in the top half to the total cpm in the whole strip.

The results, shown in FIG. 1, indicate that the preferred formulation containing 5% povidone (5% PVP) has the highest level of protein-bound $^{131}$I and further, remained above the pre-assigned product specification limit of 95% at all tested time points. More particularly, the frozen/thawed sample of the preferred 5% povidone formulation, shown as the 5* time point in FIG. 1, exhibited a protein-bound $^{131}$I level comparable to that of the room temperature samples of the preferred formulation. By contrast, the 5% HSA and the 2% PG samples showed immediate sharp declines in percentage of bound $^{131}$I starting at Day 1. These samples fared better when stored frozen and tested at Day 5 (see 5* timepoint), but such treatment reflects only a best case scenario and does not accommodate the practicalities of production, storage, and shipping.

The results of this experiment indicate that 5% povidone is superior to 5% HSA at maintaining product stability in room temperature storage for 5 days. The Day 5 ITLC values in a 5% povidone formulation are equivalent between material stored at room temperature and material in frozen storage (96.0 vs. 96.3% bound $^{131}$I). The 5% povidone formulation is also superior to 2% propylene glycol in maintaining product stability. A titration effect in the percentage povidone in this formulation was observed; as the povidone percentage decreased, there was a concomitant decrease in bound $^{131}$I values at each timepoint tested.

EXAMPLE 3

RELATIVE POTENCY OF RADIOLABELED PRODUCT IN THE PRESENCE OF DIFFERENT POVIDONE CONCENTRATIONS

B1 antibody radiolabeled with $^{131}$I was prepared and diluted to an activity concentration of 7.5 mCi/ml in various percentages of povidone. The specific activity for this preparation was 4 mCi/mg. Samples were drawn from this preparation at different time points and were tested in an IRF assay and by ITLC, as described in the previous example.

Potency and functionality of the $^{131}$I-labeled B1 antibody with different povidone concentrations was determined by the ability of the antibody to bind to its relevant antigen, CD20, in the immunoreactive fraction assay. The IRF method is a whole cell-based assay using a lyophilized cell line standard, in this case the Ball-1 cell line which expresses the CD20 antigen. At a defined concentration, $^{131}$I-labeled B1 antibody is incubated with a fixed volume of cells. The percent IRF is calculated as the fraction of the cpm from labeled antibody bound to antigen over the total amount of cpm added into the assay, (% bound cpm/total cpm)×100, with both values corrected for non-specific binding. This is the immunoreactive fraction. The percent IRF is also corrected for radiopurity as measured by ITLC. This assay is used to insure that the radiolabeling process has not diminished the biological activity of the antibody molecule. The IRF assay also serves as a measure of the stability of the radiolabeled antibody over time in a variety of storage conditions.

Figure 2:
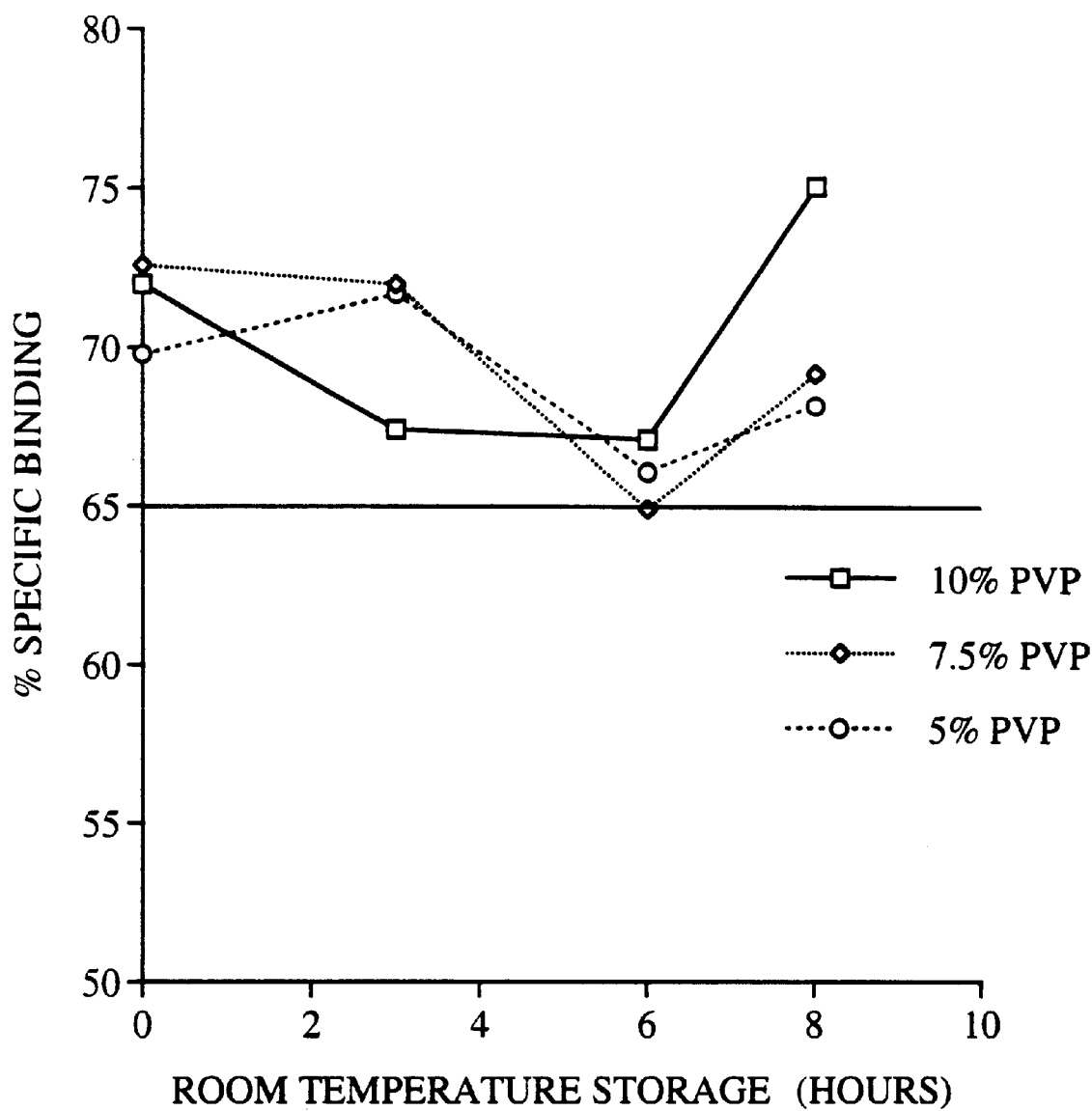
FIG. 2 is a graph showing the effectiveness of different concentrations of povidone in maintaining drug product potency at room temperature storage.

The samples were stored at room temperature for the duration of the testing. As seen in FIG. 2, formulations having 5%, 7.5%, and 10% povidone are acceptable in maintaining product potency for up to 8 hours. There are slight differences in the IRF values at each timepoint but these differences are within the range of variation expected in a cell-based assay. The largest difference occurs at the 8 hour timepoint but all values are above the pre-assigned 65% product specification limit.

The results shown in FIG. 3 reveal that the 5%, 7.5%, and 10% povidone formulations also exhibited acceptable levels of protein-bound $^{131}$I up to and including 24 hours with room temperature storage.

EXAMPLE 4

EVALUATION OF RADIOLABELED PRODUCT OF INTERMEDIATE RADIOACTIVITY LEVEL HAVING POVIDONE RADIOPROTECTANT

Radiolabeled product produced with an intermediate level of radioactivity was prepared with 5% povidone as the radioprotectant. Specifically, 54 mg of B1 antibody were labeled with 268 mCi $^{131}$I to provide a specific activity of labeling of 5 mCi/mg. The radiolabeled antibody was adjusted to an activity concentration of 6.4 mCi/ml, a specific activity of 3.6 mCi/mg, and a final antibody protein concentration of 1.7 mg/ml. The preparation was divided into 5 ml aliquots (32 mCi/vial), and some of the samples were stored frozen at −70° C. while others were held at room temperature. As before, the final product specification limit for unbound $^{131}$I was set at ≦5%.

As seen in FIG. 4, at all tested time points and at both room temperature and frozen storage, samples with 5% povidone radioprotectant exhibited stability above the pre-set product specification limits for peptide-bound $^{131}$I values. Furthermore, an IRF assay performed on a frozen/thawed sample tested on Day 5 showed a level of immunoreactivity comparable to that exhibited by a sample tested at T=0 (the first and last time points of FIG. 4).

EXAMPLE 5

RELATIVE STABILITY OF RADIOLABELED PRODUCT IN THE PRESENCE OF POVIDONE OF DIFFERENT MOLECULAR WEIGHTS

B1 i antibody was labeled with 200 mCi of $^{131}$I and diluted into 5.5% povidone comprised of either C-15 or C-30 type povidone (available from GAF Chemicals Corporation, 1361 Alps Road, Wayne, N.J.). Type C-15 povidone has a viscosity average molecular weight (Mv) of 7 kD and a K-value of K-17. Type C-30 povidone has an Mv of 38 kD and a K-value of K-30. The final activity concentration was 7.5 mCi/ml and all samples were stored at room temperature prior to testing at 0, 3, 6, 10, and 24 hours.

Stability and potency of the samples were determined using the ITLC method and the IRF assay described in Examples 2 and 3. FIGS. 5–6 show that both povidone compositions provided significant radioprotection. A gradual decrease in both protein-bound $^{131}$I values and product potency could be expected with room temperature storage of a radiolabeled product with an activity concentration of 7.5 mCi/ml. Nonetheless, this data demonstrates that povidone is effective in maintaining stability above the pre-set specification limits for up to 24 hours. A closer look at the ITLC stability data of FIG. 5 indicates that the C-15 povidone provided better protection than the C-30 material particularly at the last time point. Similarly, the IRF potency data of FIG. 6 shows that C-15 povidone is the preferred material at later time points. The C-15, or K-17, povidone is also generally preferred because the lower molecular weight allows for faster renal clearance and excretion of the povidone and decreases the possibility of toxicity.

EXAMPLE 6

RELATIVE STABILITY AND POTENCY OF POVIDONE AND POVIDONE/ASCORBIC ACID RADIOPROTECTANTS

Two separate production scale runs were performed to test the suitability of the radioprotectant in high level radioactivity fields. The first run evaluated 5.5% povidone as a radioprotectant and the second, identical run evaluated a combination 5.5% povidone and 0.1% ascorbic acid radioprotectant for effectiveness in maintaining bulk product stability at room temperature storage.

For each run, 900 mg B1 antibody was radiolabeled with 4500 mCi of $^{131}$I. For the first run evaluating povidone alone, the final product specifications were a total activity of 3735 mCi, a bulk volume of 511 mls, an activity concentration of 6.1 mCi/ml at calibration date (defined for this particular antibody/radioisotope composition as 48 hours post-manufacturing or post-radiolabeling; 7.3 mCi/ml at manufacture), a specific activity of 4.2 mCi/mg at calibration, and a protein concentration of 1.8 mg/mi. The final product specifications for the second run, evaluating the povidone/ascorbic acid radioprotectant, were a total activity of 3780 mCi, a bulk volume of 518 mls, an activity concentration of 6.1 mCi/ml at calibration (7.3 mCi/ml at manufacture), a specific activity of 4.0 mCi/mg at calibration, and a protein concentration of 1.5 mg/ml.

The radiolabeled antibody was thus stabilized with either 5.5% povidone radioprotectant or 5.5% povidone10.1% ascorbic acid radioprotectant. The bulk (high volume) fractions were held at room temperature for 180 minutes. Samples were removed from each bulk fraction at T=0, 60, 90, and 180 minutes for the performance of ITLC and IRF evaluations to determine protein-bound $^{131}$I levels and potency respectively.

FIGS. 7–8 show the relative stability and potency of the tested samples. As seen in FIG. 7, both the povidone (5.5% PVP) and the povidone/ascorbic acid (5.5% PVP/0.1% AA) formulations maintain protein-bound $^{131}$I levels above the pre-set specification limit of 95%. In FIG. 8, evidence of the comparable stability provided by the two different radioprotectants is shown at 60, 90, and 180 minutes. Because of the downward trend in potency seen between 0 and 180 minutes for the povidone formulation, it is preferred that the povidone/ascorbic acid radioprotectant be used at this level of total radioactivity and activity concentration to ensure high quality of the drug product throughout the length of a typical manufacturing run.

EXAMPLE 7

EVALUATION OF RADIOLABELED PRODUCT OF HIGH RADIOACTIVITY LEVEL HAVING POVIDONE/ASCORBIC ACID RADIOPROTECTANT

Another batch of $^{131}$I-labeled B1 antibody was produced and tested in a study designed to mimic worst-case manufacturing conditions at a large scale. The combination of 5.5% povidone and 0.1% ascorbic acid was used to maintain product stability and was added to the $^{131}$I B1 antibody by collecting the radiolabeled peptide directly from the labeling and purification apparatus into a bulk drug product bag having the radioprotectant. The total activity of this batch was 3600 mCi, a bulk volume of 480 mils, an activity concentration at calibration of 6.3 mCi/ml (7.5 mCi/ml at manufacture), a specific activity at calibration of 3.5 mCi/mg, and a protein concentration of 1.8 mg/ml.

A composition having radiolabeled antibody and radioprotectant was deliberately held at room temperature 180 minutes at the final bulk drug product step prior to dispensing into vials. Samples were removed for testing at 0, 90, and 180 minutes. Additionally, a portion of this composition was dispensed immediately and held at room temperature for 90 and 180 minutes. A sample was also removed from the bulk vessel (time=one minute, or T=1) and tested immediately. This sample served as the baseline value for the data presented below. IRF and ITLC values of the bulk and vial storage samples from the given timepoints were compared to evaluate the impact of the high radioactivity field present in the final bulk drug product vessel upon product stability and potency and to determine any deleterious effects of prolonged room temperature exposure on final drug product functionality.

TABLe 1

Stability and Potency with Povidone/Ascorbic Acid Radioprotectant for Bulk vs. Vial Storage

| Sample | ITLC-Bound $^{131}$I | IRF-% Specific Binding |
|---|---|---|
| T = I | 96.7 | 76.1 |
| T = 90/FDP Bulk | 96.8 | 72.4 |
| T = 90/Vial | 95.8 | 72.0 |
| T = 180/FDP Bulk | 96.3 | 73.8 |
| T = 180/Vial | 95.6 | 73.0 |

FDP = Final Drug Product. All samples held at room temperature.

The results in Table 1 demonstrate that potency was maintained over the three hour test period for both the final product vial and the bulk drug stage. Equivalent ITLC results demonstrate stable levels of protein-bound $^{131}$I over the three hour time period. As before, the product specification limit was set at ≧95% peptide-bound radioactivity for bound iodine and ≧65% specific binding for the immunoreactive fraction. These results demonstrated that the combination of povidone and ascorbic acid were effective in maintaining the stability of the final drug product during manufacturing and in the final vial configuration. By holding the drug product at room temperature for 90 and 180 minutes at the bulk drug product stage, rather than dispensing into vials and freezing immediately, this experiment demonstrated that the final drug product is stable at this stage for at least 3 hours using povidone/ascorbic acid radioprotectant.

EXAMPLE 8

EVALUATION OF LARGE-SCALE RADIOLABELED PRODUCT HAVING PHARMACEUTICAL GRADE POVIDONE/ ASCORBIC ACID RADIOPROTECTANT

Another production scale run with 900 mg B1 I antibody and 4500 mCi $^{131}$I was prepared with a pharmaceutical grade radioprotectant of 5–6% C-15 povidone and 0.9–1.3 mg/ml ascorbic acid. The total activity of this batch was 3735 mCi in a bulk volume of 485 mls. The activity concentration was 6.5 mCi/mi at calibration (7.7 mCi/ml at manufacture), and the specific activity was 4.2 mCi/mg at calibration. The protein concentration was 1.7 mg/ml.

In the production run, 20 dosimetric vials ($D_x$) containing 10 mCi each of $^{131}$I-labeled B1 antibody and 20 therapeutic ($R_x$) vials containing 125 mCi each of $^{131}$I-labeled B1 antibody were dispensed. Representative vials from the beginning and end of the dispensing process were tested at each timepoint. The vials were numbered sequentially according to the order in which they were filled, so lower vial numbers represent vials prepared earlier in the manufacturing and dispensing process. Storage was at ≦−70° C.

In addition to ITLC and IRF assays as described previously, HPLC was performed for information regarding the formation of aggregates. Aggregates are separated from monomeric $^{131}$I-labeled B1 antibody using size exclusion HPLC utilizing PBS buffer pH 7.0 as the mobile phase. A dual-detector system consisting of both a radiation detector and a UV-Vis monitor which can scan a sample for radiation peaks as well as UV-Vis absorbance was employed. The HPLC column separates the aggregate peaks from monomeric $^{131}$I-labeled B1 antibody, unbound iodine and other extraneous peaks. Quantification is performed by calculating the number of counts in the aggregate peaks and monomer peak as a percentage of total counts in the sample loaded on the column.

Radiolabeled final drug was held for three hours at room temperature (T=3) in the bulk drug product stage prior to dispensing and freezing to evaluate stability in comparison with material dispensed and frozen immediately (T=0) for each of the Day 1, 3, 6, and 8 time points tested. On each testing day, $R_x$ and $D_x$, as well as T=0 and T=3, representative vials were thawed and tested. A baseline sample was taken at Day 0 and diluted 1:100 in PBS+1% HSA. Radiolabeled B1 has been demonstrated to be stable in this buffer for up to 14 days at 2–8° C. The baseline sample serves as an internal control for each timepoint.

TABLE 2

Radioprotection with Povidone/Ascorbic Acid for Large-Scale Production

| Sample | Timepoint (Day) | ITLC %-Unbound $^{131}$I | IRF %-Specific Binding | HPLC %-Aggregates |
|---|---|---|---|---|
| Baseline- 1:100 | 0 | 2.1 | 79 | N.D. |
| Baseline- 1:100 | 1 | 2.5 | 77 | N.D. |
| Vial 1 T = 0 $R_x$ | 1 | 2.5 | 75 | 0.5 |
| Vial 9 T = 0 $D_x$ | 1 | 2.4 | 76 | 0.4 |
| Vial 17 T = 3 $R_x$ | 1 | 2.9 | 72 | 0.4 |
| Vial 25 T = 3 $D_x$ | 1 | 3.0 | 73 | 0.2 |
| Baseline- 1:100 | 3 | 2.7 | 73 | N.D. |
| Vial 2 T = 0 $R_x$ | 3 | 3.3 | 73 | 1.9 |
| Vial 10 T = 0 $D_x$ | 3 | 3.5 | 73 | 1.0 |
| Vial 18 T = 3 $R_x$ | 3 | 3.2 | 71 | 1.8 |
| Vial 26 T = 3 $D_x$ | 3 | 3.5 | 70 | 1.4 |
| Baseline- 1:100 | 6 | 3.3 | 73 | N.D. |
| Vial 3 T = 0 $R_x$ | 6 | 3.7 | 72 | 1.7 |
| Vial 11 T = 0 $D_x$ | 6 | 3.7 | 71 | 1.4 |
| Vial 19 T = 3 $R_x$ | 6 | 4.3 | 69 | 1.6 |
| Vial 27 T = 3 $D_x$ | 6 | 3.7 | 71 | 1.3 |
| Baseline- 1:100 | 8 | 3.5 | 73 | N.D. |
| Vial 4 T = 0 $R_x$ | 8 | 4.9 | 73 | 1.4 |
| Vial 12 T = 0 $D_x$ | 8 | 4.5 | 76 | 0.9 |
| Vial 20 T = 0 $R_x$ | 8 | 5.1 | 73 | 1.1 |
| Vial 28 T = 3 $D_x$ | 8 | 4.3 | 75 | 1.1 |

N.D. = not detectable

The final product stability was demonstrated out to 8 days by both ITLC and IRF values. As evidenced from Table 2, there were no significant differences in unbound iodine or IRF values between Day 1 and Day 8 samples, or between dosimetric ($D_x$) and therapeutic ($R_x$) dosage forms. In addition, there was minimal difference in material dispensed and frozen at T=0 and that held in the final drug product stage for 3 hours at room temperature. This study demonstrated that at the tested manufacturing scale, the combination of povidone at 5–6% w/v and ascorbic acid at 0.9–1.3 mg/ml was effective at maintaining product stability in the final dosage forms as well as in the bulk drug product stage. These results confirmed those outlined in Example 6 and make commercial production for radiolabeled peptides feasible.

EXAMPLE 9

EVALUATION OF LARGE-SCALE RADIOLABELED PRODUCT UNDER CYCLING FREEZER AND STANDARD REFRIGERATION CONDITIONS

Another production scale run with 900 mg B1 antibody and 4500 mCi $^{131}$I was prepared with a pharmaceutical grade radioprotectant of 5.5% C-15 povidone and 1.1 mg/ml ascorbic acid. The total activity of this batch was 3600 mCi in a bulk volume of 570 mls. The activity concentration was 6.3 mCi/ml at calibration (7.5 mCi/ml at manufacture), and the specific activity was 3.9 mCi/mg at calibration. The protein concentration was 1.7 mg/ml.

In the production run, dosimetric vials ($D_x$) containing 10 mCi each of $^{131}$I-labeled B1 antibody and therapeutic ($R_x$) vials containing 125 mCi each of $^{131}$I-labeled B1 antibody were dispensed. Storage was in a cycling –20° C. freezer for up to 8 days. A cycling freezer is one that warms to temperatures of 0–5° C. at defined intervals to defrost. This is a typical household style refrigerator, such as is commonly found in radiopharmacies.

Following frozen storage, on Days 2, 5 and 8, $R_x$ and $D_x$ representative vials were removed, thawed and tested. A baseline sample was taken at Day 0 and diluted 1:100 in PBS+1% HSA. Radiolabeled B1 has been demonstrated to be stable in this buffer for up to 14 days at 2–8° C. The baseline sample serves as an internal control for each timepoint Vials of both dosage forms were tested for % bound isotope (ITLC), potency (IRf) and purity (HPLC) against Day 0 release specifications (pre-set specification limits), using the ITLC method and the IRF assay described in Examples 2 and 3, and the HPLC method described in Example 8.

The final product stability under these conditions was demonstrated out to 8 days by ITLC, IRF and HPLC values. FIGS. 9–11 show that all product vials were within Day 0 release specification limits for % bound isotope, potency and purity. As seen in FIG. 9, vials of both dosage forms and the controls maintained protein-bound $^{131}$I levels above the pre-set specification limit of 95%. In FIG. 10, all product vials tested maintained specific binding levels above the pre-set specification limit of 65%. In FIG. 11, all product vials tested maintained aggregate levels below the pre-set specification limit of 5%.

In addition to the above study, product vials thawed at Day 2 were evaluated for stability post-thawing at 2–8° C. in a standard laboratory refrigerator to evaluate product stability under less desirable storage conditions. Vials of the $D_x$ and $R_x$ dosage forms were studied, along with syringe $D_x$ and $R_x$ dosage forms. Syringe $D_x$ dosage forms comprised a $D_x$ dose diluted to 30 ml in a 0.9% solution and maintained in a syringe. Syringe $R_x$ dosage forms comprised a full $R_x$ dose, undiluted and maintained in a syringe. FIGS. 12–14 show the relative stability and potency of the tested samples. Stability was defined as being within Day 0 release specification. limits for each of the stability indicating assays. Failure of any one of the assays was defined as a stability failure at a given timepoint. As seen in FIG. 12, the $D_x$ vial was stable for up to 24 hours, the $D_x$ syringe was stable for up to 48 hours, and both $R_x$ vial and syringe configurations were stable for up to 8 hours, maintaining protein-bound $^{131}$I levels above the pre-set specification limit of 95%. In FIG. 13, all the $D_x$ and $R_x$ dosage forms maintained specific binding levels above the pre-set specification limit of 65%. In FIG. 14, all the $D_x$ and $R_x$ dosage forms maintained aggregate levels below the pre-set specification limit of 5%, for up to 120 hours.

This study demonstrated that the combination of povidone at 5–6% w/v and ascorbic acid at 0.9–1.3 mg/ml was effective at maintaining product stability in the final dosage forms even under less than optimal storage conditions such as in a cycling –20° C. freezer and a standard 2–8° C. laboratory freezer, as compared to the $\leq$–70° C. storage conditions that are recommended for optimal stability.

EXAMPLE 10

EVALUATION OF LARGE-SCALE RADIOLABELED BULK DRUG PRODUCT

The stability of the $^{131}$I-labeled B1 antibody was evaluated in high radioactivity field of 50 and 70 Curies (Ci). The formulation included 12.5 mM phosphate buffered saline, 5.5% povidone and 1.1 mg/ml ascorbic acid. The radiolabeled antibody was held in a vessel at room temperature for 7 hours at an activity concentration of 8.2 mCi/mi.

Aliquots were removed at defined intervals from the vessel and tested against Day 0 release specification limits for the following stability indicating parameters: % bound isotope (ITLC), potency (IRF) and % radioactive monomer and aggregates (HPLC). The samples were evaluated using the ITLC method and the IRF assay described in Examples 2 and 3, along with the HPLC method described in Example 8.

FIGS. 15–18 show the relative stability and potency of the tested samples. As seen in FIG. 15, the 70 Ci form maintained protein-bound $^{131}$I levels above the pre-set specification limit of 95%, while the 50 Ci form maintained levels approximately at or above the 95% limit. In FIG. 16, both the 50 Ci and 70 Ci forms maintained specific binding levels above the pre-set specification limit of 65%. In FIG. 17, both forms maintained % radioactive monomer levels above the pre-set specification limit of 95%. In FIG. 18, both forms maintained aggregate levels below the pre-set specification limit of 5%.

This study demonstrates that the radioprotectant of the invention provides excellent results even for a radiolabeled peptide having a very high radioactivity level. The $^{131}$I-labeled B1 antibody drug product was stable out to 7 hours at room temperature with minimal changes observed in any of the stability indicating parameters across the duration of the testing period.

EXAMPLE 11

PHARMACOKINETIC EQUIVALENCE OF RADIOLABELED PRODUCT WITH POVIDONE/ASCORBIC ACID RADIOPROTECTANT AND WITH HSA

An animal study was performed to demonstrate that a formulation having a povidone/ascorbic acid radioprotectant did not alter the pharmacokinetic and tissue biodistribution characteristics of a particular radiolabeled peptide as compared to a formulation using an HSA radioprotectant.

Normal Swiss/Webster mice were tested to compare the blood and tissue binding and clearance profiles for preparations of radiolabeled Anti-CD20 antibody, particularly B1 antibody having different radioprotectants. One sample utilized povidone/ascorbic acid for radioprotection and another utilized HSA for radioprotection. Additionally, one of the samples was labeled with $^{131}$I, while the other sample was labeled with $^{125}$I having the same specific activity of labeling (5 mCi/mg) as the $^{131}$I-labeled sample. The $^{125}$I-labeled sample was thus formulated in Phosphate Buffered Saline (PBS)/15% HSA and the $^{131}$I-labeled sample was formulated in PBS/5.5% povidone with 0.1% ascorbic acid.

The dual-label study allows both the $^{125}$I-labeled and $^{131}$I-labeled Anti-CD20 Antibody preparations to be administered intravenously into the same animal to facilitate comparisons and overcome the innate differences in clearance of antibodies between individual animals. The different decay properties of the two radioisotopes allowed simultaneous collection of data at each time point.

Each time point group consisted of six animals and the data is presented as the mean counts from within each group. The standard error of the mean within each time point group was typically less than 5% for this study. The study was divided into two arms to test for equivalence of delivery to specific tissues and for equivalence of blood clearance rates.

Each mouse was injected with approximately $10^7$ counts per minute (cpm) of $^{125}$I-labeled antibody and $5 \times 10^6$ cpm of $^{131}$I-labeled antibody to facilitate the approximately 20.2% cross-over correction in the counting windows between the two radioisotopes. The labeled antibodies correspond to a protein dose of 1 μg each. The total injected protein dose was adjusted by the addition of 100 μg of unlabeled antibody per mouse. The final injected dose was an equi-volume mixture of the $^{125}$I-labeled and $^{131}$I-labeled antibody solutions. The final injected dose of $^{131}$I/$^{125}$I-labeled antibody mixture therefore contained 2.75% povidone, 0.05% ascorbic acid, and 2.5% HSA. The data presented in Table 3 and FIG. 19 are derived from samples counted at the end of the study to minimize errors due to the differences in decay rates for the two radionuclides. The mice in this study exhibited no overt signs of toxicity and remained healthy until they were sacrificed.

Equivalence of Distribution in Specific Tissues

The injected animals were sacrificed at various time points and selected tissues taken for the determination of percent injected dose (% ID) per gram of tissue. For this calculation, whole organs were removed at sacrifice, weighed and counted in a gamma well counter. The percent injected dose (%ID) per gram is calculated as a percentage of the total cpm injected using individual standards prepared for each radiolabeled antibody.

TABLE 3

Ratio of % Injected Dose (I.D.)/Gram $^{125}$I(HSA): $^{131}$I(PVP/AA) B1 Antibody in Normal Mice

| | Time points (hours) | | | | | |
|---|---|---|---|---|---|---|
| Organs | 0    1 | 24 | 48 | 96 | 168 | 216 |
| Blood | 0.92    1.00 | 1.01 | 1.06 | 1.09 | 1.09 |
| Liver | 0.87    0.97 | 1.17 | 1.03 | 1.10 | 1.06 |
| Spleen | 0.92    1.02 | 1.04 | 1.08 | 1.11 | 1.15 |
| Kidneys | 0.91    1.01 | 1.04 | 1.07 | 1.10 | 1.09 |
| Heart | 0.99    1.04 | 1.07 | 1.10 | 1.13 | 1.12 |
| Lungs | 0.94    1.03 | 1.05 | 1.09 | 1.11 | 1.14 |
| Muscle | 0.95    1.03 | 1.04 | 1.08 | 1.11 | 1.09 |
| L. Femur | 0.93    0.99 | 1.03 | 1.05 | 1.06 | 1.06 |

Table 3 compares the blood and tissue biodistribution of the two preparations of anti-CD20 antibody over a nine day period. The data are presented as the ratio of the residual amount of each of the preparations found at each tissue at the time the animal was sacrificed. More particularly, the percent injected dose per gram tissue weight for each tissue and each antibody preparation is obtained and the comparison is presented as a ratio of $^{125}$I-labeled antibody (HSA formulation) to $^{131}$I-labeled antibody (povidone/ascorbic acid formulation).

For nearly all tissues and all time points, the ratio was 1.0±0.1, indicating nearly identical clearance rates between the two radiolabeled antibody preparations. There are several points outside this range, but these points fall within the range of variability for this type of analysis.

The volume of antibody solution containing 5.5% povidone and 0.1% ascorbic acid that is administered to each animal is equivalent to 2–3% of the total blood volume of a 20 gram mouse. On a per volume basis comparison to an average total human blood volume, this would be approximately equivalent to 100 ml of 5.5% povidone and 0.1% ascorbic acid or approximately three times higher than proposed in the method described in U.S. Pat. No. 5,595,721.

Equivalence of Blood Clearance Rates

In a parallel experiment, the injected animals were bled at several time points (5 1 per bleed) and ultimately sacrificed at the final 216 hour time point for the determination of blood clearance profiles.

As shown in FIG. 19, greater than 50% of the injected dose is cleared from the blood within 24 hours post-injection for both $^{131}$I-labeled and $^{125}$I-labeled antibody preparations. There is a slight divergence of the curves starting at 24 hours, but when the individual data points are analyzed, they differ by less than five percentage points for all time points tested. An unpaired, two-tailed student t-test of these values gave a p-value of 0.9288, indicating no significant difference between the two curves. As can be seen in FIG. 19, the $^{131}$I material appears to be clearing from the blood at a slightly faster rate than the $^{125}$I labeled antibody. These differences, however, are not significant and fall within the range of variability for this type of in vivo biodistribution assay.

These results indicated again that the, povidone/ascorbic acid radioprotectant did not alter the blood clearance of the radiolabeled anti-CD20 antibody.

All publications and patent applications mentioned in this specification are herein incorporated by reference to the same extent as if each individual publication or patent application was specifically and individually indicated to be incorporated by reference.

What is claimed is:

1. A stable peptide-radioisotope composition comprising:
   radiolabeled peptides,
   povidone, and
   a secondary stabilizer selected from ascorbic acid, benzyl alcohol, cysteamine, cystamine, propylene glycol, dextran, and gentisic acid,
   wherein the povidone and secondary stabilizer are present in an amount sufficient to ameliorate degradation of the peptides by radioactivity and further wherein the radiolabeled peptides provide a total radioactivity field of up to approximately 70 Ci.

2. The composition of claim 1 wherein the secondary stabilizer is ascorbic acid and further wherein the ascorbic acid is present at 10 mg/ml or less of the composition.

3. The composition of claim 1 wherein the povidone is present in a range of 0.5–10% w/v of the composition.

4. The composition of claim 1 wherein the composition provides an activity concentration of 10 mCi/ml or less.

5. The composition of claim 1 wherein the radiolabeled peptide is an antibody.

6. The composition of claim 1 wherein the radiolabeled peptide is radiolabeled with a radioisotope having emissions selected from β particles, photons, α particles, Auger electrons, and internal conversion electrons.

7. The composition of claim 1 wherein the radiolabeled peptides is radiolabeled with a radioisotope selected from $^{111}$In, $^{67}$Ga, $^{90}$Y, $^{131}$I, $^{125}$I, $^{123}$I, $^{32}$P, $^{47}$Sc, $^{67}$Cu, $^{90}$Y, $^{109}$Pd, $^{111}$Ag, $^{153}$Sm, $^{166}$Ho, $^{177}$Lu, $^{186}$Re, $^{188}$Re, $^{199}$Au, $^{211}$At, $^{212}$Bi, $^{223}$Ra, $^{225}$Ac, $^{213}$Bi, $^{99m}$Tc.

8. The composition of claim 1 wherein the radiolabeled peptide is radiolabeled by a method selected from covalent labeling, direct substitution, and chelation.

9. The composition of claim 1 wherein the radiolabeled peptide exists as a physical mixture of the peptide and a radioisotope.

10. A radioprotectant for ameliorating degradation of radiolabeled peptides comprising:
    a stabilizer solution comprising povidone and a secondary stabilizer selected from ascorbic acid, benzyl alcohol, cysteamine, cystamine, propylene glycol, dextran, and gentisic acid,
    wherein the radioprotectant ameliorates degradation of radiolabeled peptides that provide a total radioactivity field of up to approximately 70 Ci.

11. The radioprotectant of claim 10 wherein the secondary stabilizer is ascorbic acid and further wherein the ascorbic acid is present at 10 mg/ml or less of a composition comprising a radiolabeled peptide and the stabilizer solution.

12. The radioprotectant of claim 10 wherein the povidone is present in a range of 0.5–10% w/v of a composition comprising a radiolabeled peptide and the stabilizer solution.

13. The radioprotectant of claim 10, wherein the radiolabeled peptides have an activity concentration of 10 mCi/ml or less.

14. The radioprotectant of claim 10 wherein the radiolabeled peptides are radiolabeled with a radioisotope selected from $^{111}$In, $^{67}$Ga, $^{90}$Y, $^{131}$I, $^{125}$I, $^{123}$I, $^{32}$P, $^{47}$Sc, $^{67}$Cu, $^{90}$Y, $^{109}$Pd, $^{111}$Ag, $^{153}$Sm, $^{166}$Ho, $^{177}$Lu, $^{186}$Re, $^{188}$Re, 199Au, $^{211}$At, $^{212}$Bi, $^{223}$Ra, $^{225}$Ac, $^{213}$Bi, and $^{99m}$Tc.

15. A method for making a stable peptide-radioisotope composition, the method comprising:
    labeling a peptide with a radioisotope, and
    contacting the labeled peptide with povidone and a secondary stabilizer selected from ascorbic acid, benzyl alcohol, cysteamine, cystamine, propylene glycol, dextran, and gentisic acids
    wherein the composition provides a total radioactivity field of up to approximately 70 Ci.

16. The method of claim 15 wherein the labeled peptide provides an activity concentration of 10 mCi/ml or less.

17. The method of claim 15 wherein the secondary stabilizer is ascorbic acid and further wherein the ascorbic acid is present at 10 mg/ml or less of the composition.

18. The method of claim 15 wherein the povidone is present in a range of 0.5–10% w/v of the composition.

19. The method of claim 15 wherein the peptide is labeled with a radioisotope having emissions selected from β particles, photons, α particles, Auger electrons, and internal conversion electrons.

20. The method of claim 15 wherein the peptide is labeled with a radioisotope selected from $^{111}$In, $^{67}$Ga, 90Y, $^{131}$I, $^{125}$I, $^{123}$I, $^{32}$P, $^{47}$SC, $^{67}$Cu, $^{90}$Y, $^{109}$Pd, $^{111}$Ag, $^{153}$Sm, $^{166}$Ho, $^{177}$Lu, $^{186}$Re, $^{188}$Re, 199Au, $^{211}$At, $^{212}$Bi, $^{223}$Ra, $^{225}$Ac, $^{213}$Bi, and $^{99m}$Tc.

21. The composition of claim 1 wherein the composition is suitable for administration to a patient.

22. The radioprotectant of claim 10 wherein the radioprotectant is suitable for administration to a patient.

23. The method of claim 15 wherein the composition is suitable for administration to a patient.

* * * * *